(12) United States Patent
Sartbaeva et al.

(10) Patent No.: US 10,881,620 B2
(45) Date of Patent: Jan. 5, 2021

(54) BIOMOLECULE PRESERVATION

(71) Applicant: UNIVERSITY OF BATH, Bath (GB)

(72) Inventors: Asel Sartbaeva, Bath (GB); Stephen Wells, Bath (GB)

(73) Assignee: UNIVERSITY OF BATH, Bath (GB)

(*) Notice: Subject to any disclaimer, the term of this patent is extended or adjusted under 35 U.S.C. 154(b) by 0 days.

(21) Appl. No.: 16/322,312

(22) PCT Filed: Aug. 3, 2017

(86) PCT No.: PCT/GB2017/052260
§ 371 (c)(1),
(2) Date: Jan. 31, 2019

(87) PCT Pub. No.: WO2018/025044
PCT Pub. Date: Feb. 8, 2018

(65) Prior Publication Data
US 2019/0167600 A1 Jun. 6, 2019

(30) Foreign Application Priority Data
Aug. 4, 2016 (GB) .................................. 1613476.9

(51) Int. Cl.
A61K 9/51 (2006.01)
A61K 9/50 (2006.01)
(Continued)

(52) U.S. Cl.
CPC ............. A61K 9/51 (2013.01); A61K 9/0053 (2013.01); A61K 9/2036 (2013.01); A61K 9/501 (2013.01);
(Continued)

(58) Field of Classification Search
None
See application file for complete search history.

(56) References Cited

U.S. PATENT DOCUMENTS 5,063,179 A * 11/1991 Menashi ................. C01B 33/12
423/335
9,265,729 B2 * 2/2016 Nakamura ............. C08G 77/06
(Continued)

FOREIGN PATENT DOCUMENTS

WO WO 2004/103351 A1 12/2004
WO WO 2005/007284 A2 1/2005
(Continued)

OTHER PUBLICATIONS

M Mahkam. "Synthesis and Characterization of pH-Sensitive Silica Nanoparticles for Oral-Insulin Delivery." Current Drug Delivery, vol. 8, 2011, pp. 607-611. (Year: 2011).*
(Continued)

Primary Examiner — Isaac Shomer
(74) Attorney, Agent, or Firm — Burns & Levinson, LLP; Daniel W. Clarke

(57) ABSTRACT

The present invention provides a way to capture a biomolecule such as a protein in one or more layers of covalently bonded amorphous silica, forming a cage or shell which preserves the shape of the protein and prevents denaturation caused by heat and/or aging and/or non-physiological conditions, through unfolding and loss of secondary and/or higher order structure.

21 Claims, 11 Drawing Sheets

Figure 1A:
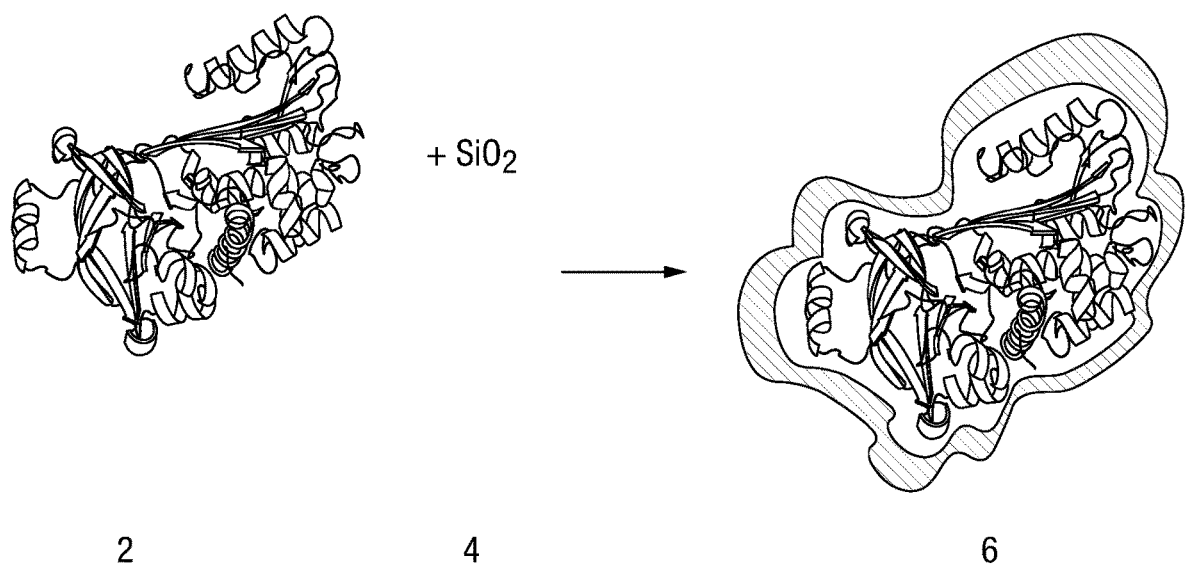

(51) Int. Cl.
| | |
|---|---|
| A61K 39/00 | (2006.01) |
| B82Y 5/00 | (2011.01) |
| A61K 39/08 | (2006.01) |
| A61K 9/00 | (2006.01) |
| A61K 9/20 | (2006.01) |
| A61K 39/39 | (2006.01) |

(52) U.S. Cl.
CPC ............ *A61K 9/5115* (2013.01); *A61K 39/00* (2013.01); *A61K 39/08* (2013.01); *A61K 39/39* (2013.01); *A61K 2039/542* (2013.01); *A61K 2039/60* (2013.01); *B82Y 5/00* (2013.01)

(56) References Cited

U.S. PATENT DOCUMENTS

| | | | | |
|---|---|---|---|---|
| 2005/0147752 | A1* | 7/2005 | Kodas | A61K 6/0276 427/249.1 |
| 2006/0280799 | A1* | 12/2006 | Tirelli | A61K 9/5089 424/489 |
| 2008/0286371 | A1* | 11/2008 | Pacheco | A61K 9/1611 424/491 |
| 2011/0229576 | A1* | 9/2011 | Trogler | A61K 9/0019 424/490 |
| 2013/0274226 | A1* | 10/2013 | Cheng | A61K 49/0032 514/63 |
| 2014/0271481 | A1* | 9/2014 | Boday | A61K 49/0054 424/9.6 |
| 2016/0015652 | A1* | 1/2016 | John | C09B 11/24 424/490 |
| 2016/0108244 | A1* | 4/2016 | Kane | C09B 67/0007 106/287.12 |
| 2020/0222557 | A1* | 7/2020 | Berlin | A61K 38/191 |

FOREIGN PATENT DOCUMENTS

| | | |
|---|---|---|
| WO | WO 2008/018716 A1 | 2/2008 |
| WO | WO 2014/172685 A1 | 10/2014 |
| WO | WO-2015089590 A1 * | 6/2015 ............ A61K 39/12 |

OTHER PUBLICATIONS

Agency for Toxic Substances and Disease Registry. Hydrogen Fluoride. https://www.atsdr.cdc.gov/mhmi/mmg11.pdf accessed May 13, 2019, 24 printed pages (numbered 1-23 and then a second page 23). (Year: 2019).*

Y Urabe, T Shiomi, T Itoh, A Kawai, T Tsunoda, F Mizukami, K Sakaguchi. "Encapsulation of Hemoglobin in Mesoporous Silica (FSM)—Enhanced Thermal Stability and Resistance to Denaturants." ChemBioChem, vol. 8, 2007, pp. 668-674. (Year: 2007).*

X Zhao, C Shan, Y Zu, Y Zhang, W Wang, K Wang, X Sui, R Li. "Preparation, characterization, and evaluation in vivo of Ins-SiO2-HP55 (insulin-loaded silica coating HP55) for oral delivery of insulin." International Journal of Pharmaceutics, vol. 454, 2013, pp. 278-284. (Year: 2013).*

T Andreani, et al. "Surface engineering of silica nanoparticles for oral insulin delivery:Characterization and cell toxicity studies." Colloids and Surfaces B: Biointerfaces, vol. 123, 2014, pp. 916-923. (Year: 2014).*

L Tang, J Cheng. "Nonporous silica nanoparticles for nanomedicine application." Nano Today, vol. 8, 2013, pp. 290-312. (Year: 2013).*

Z Xu, S Liu, Y Kang, M Wang. "Glutathione- and pH-responsive nonporous silica prodrug nanoparticles for controlled release and cancer therapy." Nanoscale, vol. 7, 2015, pp. 5859-5868. (Year: 2015).*

S Begu, S Girod, DA Lerner, N Jardiller, C Tourne-Peteilh, J-M Devoisselle. "Characterization of a phospholipid bilayer entrapped into non-porous silica nanospheres." Journal of Materials Chemistry, vol. 14, 2004, pp. 1316-1320. (Year: 2004).*

C Oh, J-H Lee, Y-G Lee, Y-H Lee, J-W Kim, H-H Kang, S-G Oh. "New approach to the immobilization of glucose oxidase on non-porous silica microspheres functionalized by (3-aminopropyl)trimethoxysilane (APTMS)." Colloids and Surfaces B: Biointerfaces, vol. 53, 2006, pp. 225-232. (Year: 2006).*

SJ Soenen, B Manshian, SH Doak, SC De Smedt, K Braeckmans. "Fluorescent non-porous silica nanoparticles for long-term cell monitoring: Cytotoxicity and particle functionality." Acta Biomaterialia, vol. 9, 2013, pp. 9183-9193. (Year: 2013).*

K-W Hu, K-C Hsu, C-S Yeh. "pH-Dependent biodegradable silica nanotubes derived from Gd(OH)3 nanorods and their potential for oral drug delivery and MR imaging." Biomaterials, vol. 31, 2010, pp. 6843-6848, available online Jun. 12, 2010. (Year: 2010).*

S-H Wu, C-Y Moua and H-p. Lin. "Synthesis of mesoporous silica nanoparticles." Chemical Society Reviews, vol. 42, 2013, pp. 3862-3875. (Year: 2013).*

Lorena Betancor and Heather R. Luckarift. "Bioinspired enzyme encapsulation for biocatalysis." Trends in Biotechnology vol. 26 No. 10, 2008, pp. 566-572. (Year: 2008).*

LM Ellerby, CR Nishida, F Nishida, SA Yamanaka, B Dunn, JS Valentine, JI Zink. "Encapsulation of Proteins in Transparent Porous Silicate Glasses Prepared by the Sol-Gel Method." Science, vol. 255, 1992, pp. 1113-1115. (Year: 1992).*

D Liu, X He, K Wang, C He, H Shi, L Jian. "Biocompatible Silica Nanoparticles—Insulin Conjugates for Mesenchymal Stem Cell Adipogenic Differentiation." Bioconjugate Chem. 2010, 21, 1673-1684. (Year: 2010).*

N Dwivedi, MA Arunagirinathan, S Sharma, and J Bellare. "Silica-Coated Liposomes for Insulin Delivery." Hindawi Publishing Corporation, Journal of Nanomaterials vol. 2010, Article ID 652048, pp. 1-8. (Year: 2010).*

SS Bale, SK Kwon, DA Shah, A Bannerjee, JS Dordick, RS Kane. "Nanoparticle-Mediated Cytoplasmic Delivery of Proteins To Target Cellular Machinery." ACS Nano, vol. 4, No. 3, 2010, pp. 1493-1500. (Year: 2010).*

A Cao, Z Ye, Z Cai, E Dong, X Yang, G Liu, X Deng, Y Wang, S-T Yang, H Wang, M Wu, Y Liu. "A Facile Method to Encapsulate Proteins in Silica Nanoparticles: Encapsulated Green Fluorescent Protein as a Robust Fluorescence Probe." Angew. Chem. Int. Ed. 2010, vol. 49, pp. 3022-3025. (Year: 2010).*

Gordon, S., et al., "In Vitro and In Vivo Investigation of Thermosensitive Chitosan Hydrogels Containing Silica Nanoparticles for Vaccine Delivery", European Journal of Pharmaceutical Sciences, 2010, vol. 41, pp. 360-368.

* cited by examiner

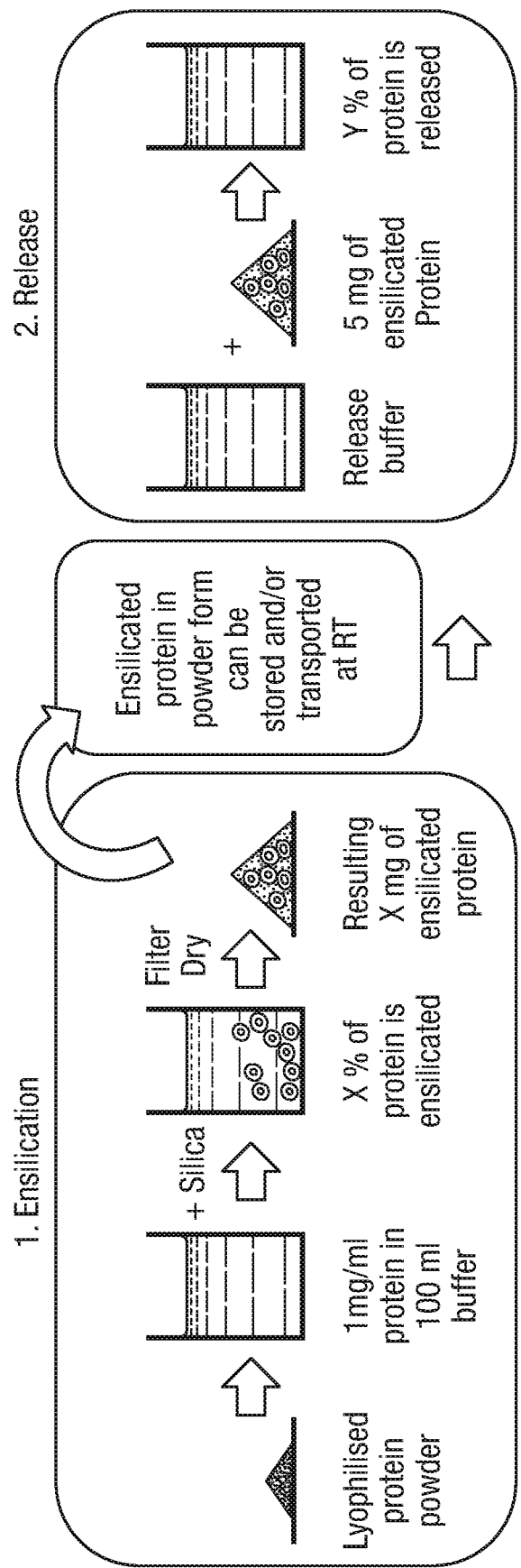

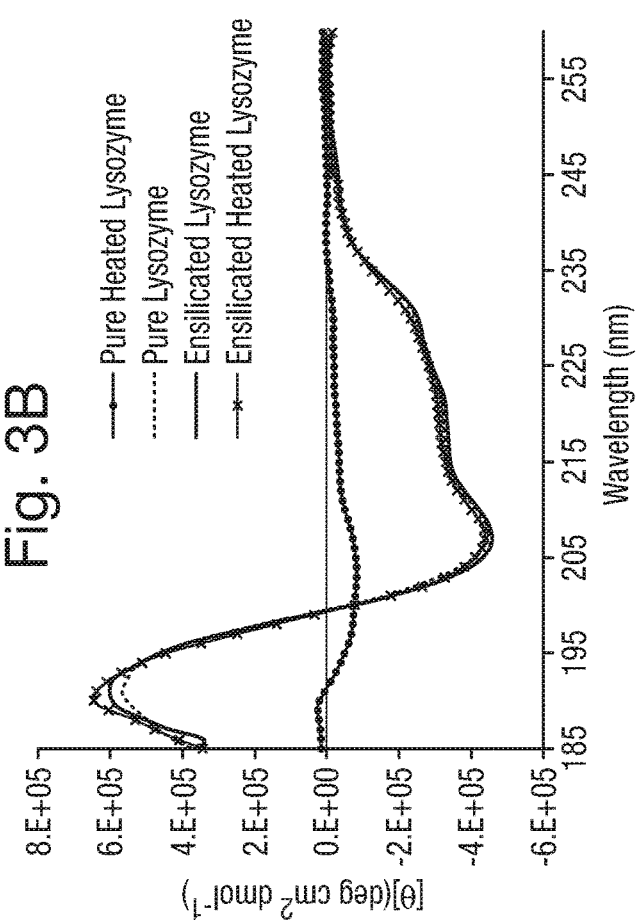
Fig. 3A
Fig. 3B
Fig. 3D
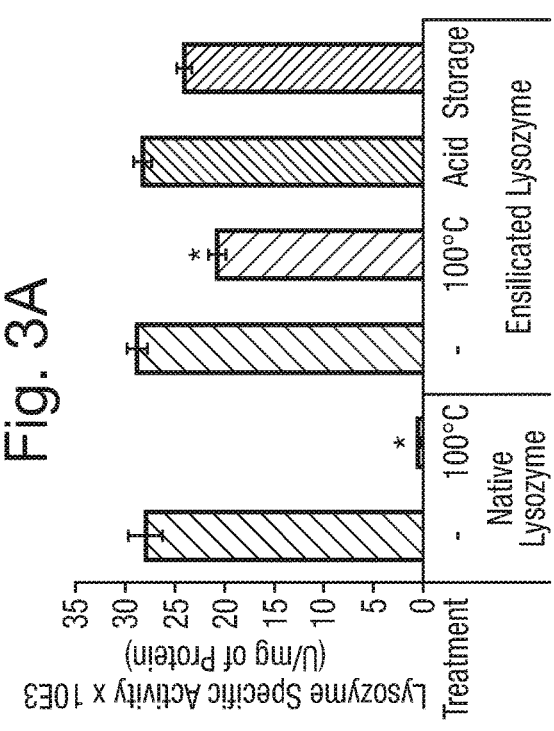
Fig. 3C

Fig. 11

in 40 s);

BIOMOLECULE PRESERVATION

CROSS-REFERENCES TO RELATED APPLICATIONS

This application is a national stage application, filed under 35 U.S.C. § 371, of International Application No. PCT/GB2017/052260, filed Aug. 3, 2017, which claims the benefit of priority under 35 U.S.C. § 119 to Great Britain Patent Application No. 1613476.9, filed Aug. 4, 2016, each of which is incorporated herein by reference in its entirety.

INTRODUCTION

Many biomolecules have specific shapes and configurations necessary for their activity. Such biomolecules include vaccines, antibodies, enzymes and other protein based active compounds. Loss of their specific shape or configuration leads to loss of function.

Biomolecules typically degrade at room temperature over time due to denaturation of proteins, which unfold with loss of secondary and tertiary structure. Higher temperatures cause more rapid denaturation. Their storage and distribution therefore relies on a "cold chain" of continuous refrigeration. Use of a cold chain is costly. It was estimated by UNICEF in 2012 that 95% of their expenditure on vaccines was spent on cold chain and transport. Furthermore, breaks in the cold chain can occur due to factors such as inconsistent supply of electricity needed to power refrigeration, or because some areas are not accessible by refrigerated vehicles meaning vaccines are carried in insulated boxes by foot, bicycle, or on animals. Breaks in the cold chain lead to rapid loss of effectiveness and potency. For example, measles live attenuated virus (LAV) vaccine is stable for two years if kept at 2-8° C., but loses 50% potency after 1 hour at 22° C. and loses 100% potency after 1 hour at 37° C. As a further example the tuberculosis vaccine BOG is stable for one year if kept at 2-8° C. but loses 50% potency after 30 minutes above 22° C. It is estimated that up to 40% of vaccines worldwide are lost or become ineffective before use due to denaturation.

Efforts have been made to make vaccines thermally stable using treatments including freeze-drying (lyophilisation). However many vaccines include adjuvants, for example alum, which cannot be freeze-dried (lyophilised).

Therefore there is a need to store and transport biomolecules in a way which protects them from denaturation and removes the reliance on cold chain.

SUMMARY

Figure 9:
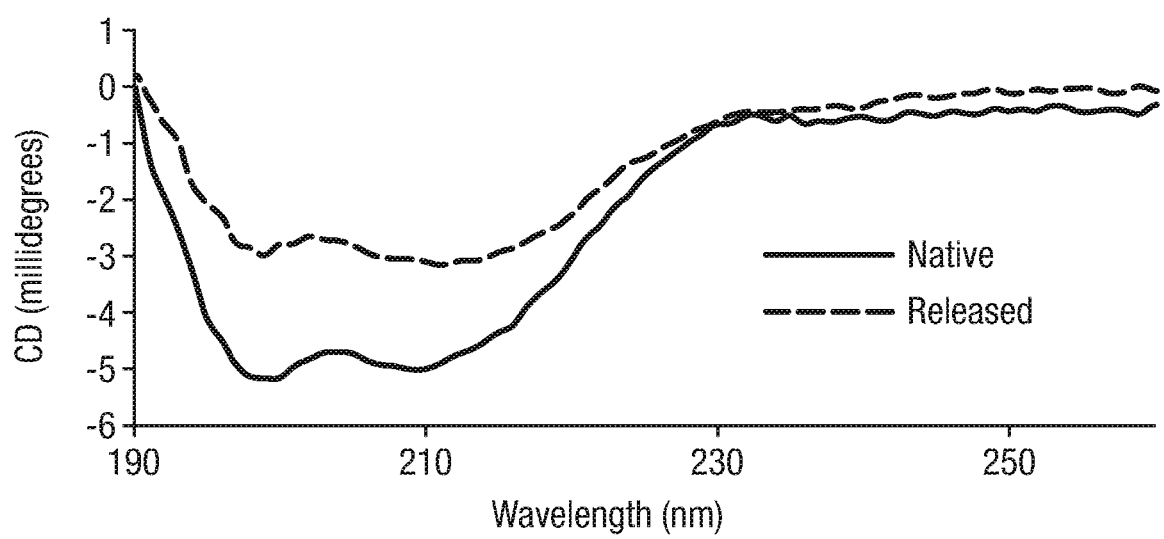

The present invention provides a way to capture a biomolecule such as a protein in one or more layers of covalently bonded amorphous silica, forming a cage or shell which preserves the shape of the protein and prevents denaturation caused by heat and/or aging and/or non-physiological conditions, through unfolding and loss of secondary and/or higher order structure.

FIGURES

FIG. 1A schematically shows enveloping a biomolecule 2 with silica 4 to produce a biomolecule enveloped with silica 6.

FIG. 1B schematically shows biomolecule ensilication and release.

FIG. 2 shows formation of ensilicated powder.

A Illustration of the ensilication. Left beaker contains protein solution, right beaker—protein solution with prehydrolysed TEOS after the formation of the silica precipitated; B DLS spectra for native lysozyme (----), and immediately after addition of TEOS (—=in 20 s, —*— in 30 s, —■— in 40 s);

C TEM images of ensilicated lysozyme powder with magnification $250\times10^3$. Scale bar equals 100 nm;

D FT-IR spectra for native lysozyme (----), silica (—) and ensilicated lysozyme (—). The bands at 1652, 1538, 1255 $cm^{-1}$ correspond to amide I, amide II and amide III groups in lysozyme and the bands at 1063 and 972 $cm^{-1}$ correspond to Si—O—Si stretching and Si—O bending.

FIG. 3: Characterisation of the ensilicated and released lysozyme.

A Specific activity of lysozyme protein before and after ensilication. Ensilicated lysozyme powder was treated by heating at 100° C. for 5 h, by incubating in 10 N HCl for 3 h, or stored at 22° C. for 6 months. At the end of the treatment, the ensilicated lysozyme was released and the lysozyme activity measured. Data are mean and SEM, n=3, *p<0.05.

B CD spectra for lysozyme (—●— - unprotected heated lysozyme, —- native lysozyme, * * * — ensilicated lysozyme, —*— - ensilicated heated lysozyme);

C SDS-PAGE analysis of lysozyme. Lanes 1-3: ensilicated lysozyme (3 individual preparations), Lanes 4-6: ensilicated heated lysozyme (3 individual preparations), Lane 7: heated unprotected lysozyme solution, Lane 8: native lysozyme solution (a control), Lane 9: dry-heated lyophilised lysozyme, Lanes 10-12: ensilicated acid treated lysozyme (3 individual preparations), Lane 13: supernatant after ensilication.

D Ribbon diagram of the crystal structure of the released lysozyme (green) superimposed onto a published structure of the protein (red; PDB code 2w1x). Rmsd overall 0.09 Å. Rmsd individual amino acids 0.24 Å.

FIG. 4 Shows structural data for ensilication of haemoglobin (Hb).

B FT-IR data for Hb, silica, and ensilicated Hb (native Hb=---, silica=········ and enslicated Hb=—. The bands are as described in FIG. 2D.

A Circular dichroism data on Hb samples: native Hb (········), ensilicated Hb (—), Hb released from ensilication after heat treatment (—*—), and pure Hb after heat treatment ( * * * ).

FIG. 5. Mass spectrometry analysis of lysozyme before A and after ensilication B.

FIG. 6. Lysozyme activity assay of lysozyme absorbed onto silica or ensilicated lysozyme that has not been released. Native lysozyme solution (1 mg/ml) was used as a control.

FIG. 7. SDS-PAGE and Western Blot of recombinant tetanus toxin C-fragment (rTTCF). SDS-Page of rTTCF confirms molecular weight (~52 kDa) and release from silica (left) where Western Blot supports this evidence in histidine residue verification (right). No degradation products were observed from released sample.

FIG. 8. UV-vis of rTTCF aqueous and in silica.

UV-vis analysis of rTTCF in native, silica and released forms show peaks at 280 and 230 nm representing protein bonds and tertiary structure UV absorption respectively. Silica in powdered form was used as a control.

FIG. 9. Circular Dichroism of TTCF.

CD indicates similar protein asymmetry patterns for both samples.

Figure 10:
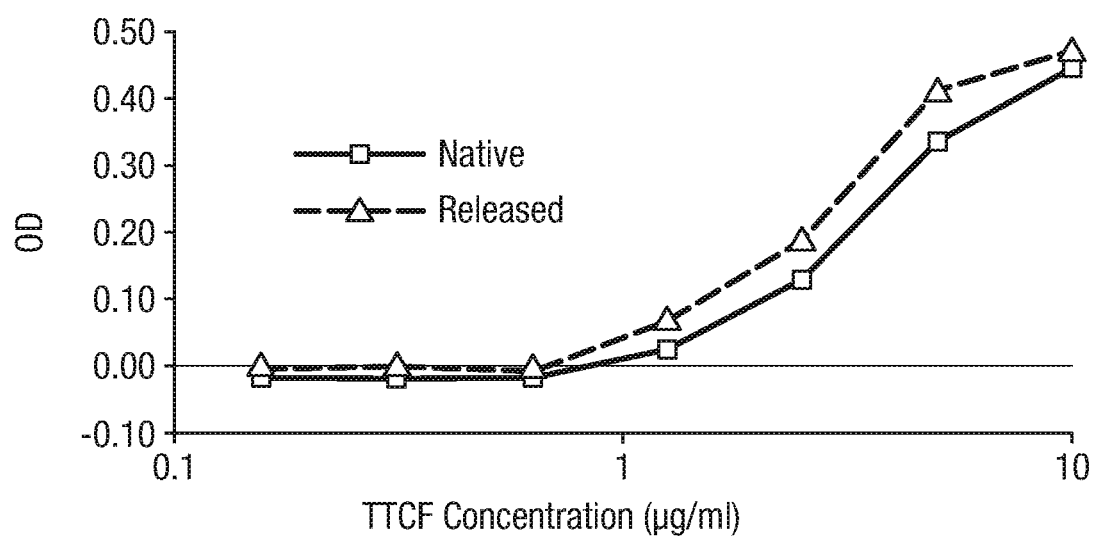

FIG. 10. ELISA of rTTCF.

ELISA results show similar binding patterns between native and release implying no alteration of antibody binding sites.

Figure 11:
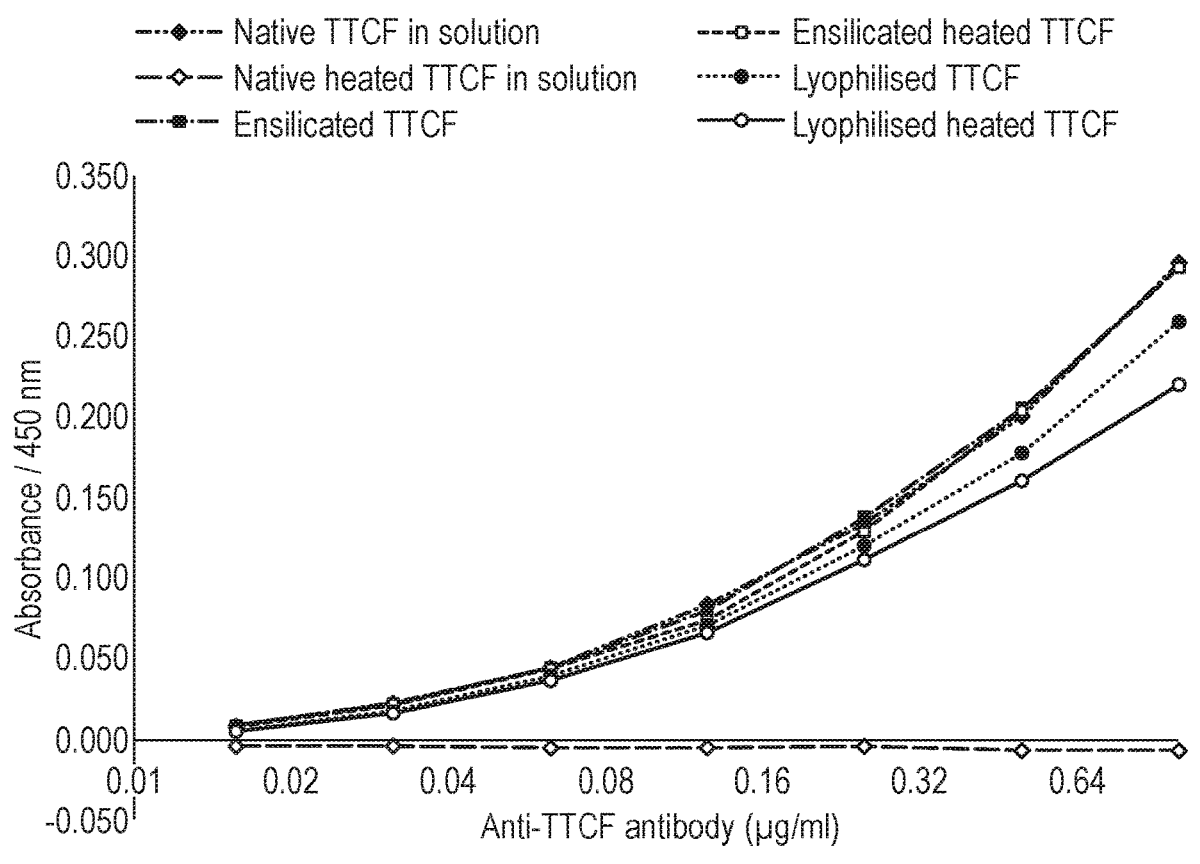

FIG. 11. shows a comparison of antibody binding capacity of lyophilised recombinant TTCF, ensilicated TTCF and recombinant TTCF in solution.

DESCRIPTION

In one aspect the present invention provides a biomolecule enveloped with silica. The biomolecule may be caged by silica. This is referred to herein as a biomolecule being "ensilicated" and the process is referred to as "ensilication". The silica envelope or cage physically prevents the biomolecule from denaturing, or from loss of shape and structure, or from unfolding. The silica envelope or cage can shield or separate the biomolecule from potentially denaturing conditions. This can also be understood as physical entrapment of a biomolecule in its native structure within a polymerized matrix of silica.

The silica envelope shields or separates the biomolecule from potentially denaturing conditions.

The potentially denaturing conditions can include heat. An ensilicated biomolecule according to the present invention can be subjected to 100° C. for 1 minute or longer such as 2, 3, 4, 5, 6, 10, 12, 15, 20, 30, 45, 60 or 90 minutes, 2 hours, 3 hours, 4 hours or even 5 hours. When subsequently released from ensilication the biomolecule is substantially intact and substantially functional. By contrast a biomolecule that is not ensilicated (unless from a thermophile) would be denatured and lose its function.

The potentially denaturing conditions can include acid pH. An ensilicated biomolecule according to the present invention can be subjected to low pH such as ≤pH 4.0, ≤pH 3.5 or ≤pH 3.0. When subsequently released from ensilication the biomolecule is substantially intact and substantially functional. By contrast a biomolecule that is not ensilicated (unless evolved to be specifically acid resistant like a digestive enzyme) would be denatured and lose its function.

The potentially denaturing conditions can include aging and storage. An ensilicated biomolecule according to the present invention can be kept or stored for a month, 2, 3, 4, 5 or 6 months or longer. When subsequently released from ensilication the biomolecule is substantially intact and substantially functional. By contrast a biomolecule that is not ensilicated would become denatured and lose its function.

Since the silica envelope shields or separates the biomolecule from potentially denaturing conditions the silica envelope shields or separates the biomolecule from surrounding conditions.

An ensilicated biomolecule is separated by the silica envelope from other molecules. An ensilicated biomolecule is separated by the silica envelope from having activity or performing its function. When subsequently released from ensilication the biomolecule can perform its activity or function. For example an ensilicated enzyme cannot be act on its substrate, an ensilicated ligand cannot bind its receptor, an ensilicated antibody cannot bind its antigen and vice versa.

Organisms such as nettles, diatoms and radiolaria use nanoscale silica structures for protection. Previous work involving silica and biomolecules, such as proteins, has not aimed at or achieved preventing the biomolecule from denaturing, or from losing their shape and structure, or from unfolding. Such previous work has included deposition of proteins in the large, open pores of a previously prepared porous silica gel, deposition of proteins on the surface of preformed silica nanoparticles, and deposition of protein on a flat silica surface followed by further silica deposition on the surface, creating a partially shape-specific protein-holding site. Each of those methods results in a protein that is exposed or at least partially exposed to its surrounding, potentially denaturing, conditions. Furthermore none of those methods creates an envelope or cage that holds a biomolecule in its folded structure.

Some previous work involving silica and biological entities has involved creating a discontinuous silica exterior on a virus. In such examples the virus can function and have infectivity with the silica exterior in place. As such the discontinuous silica exterior does not separate a virus from surrounding conditions.

Some previous work involving silica and biological entities has involved entrapment of enzymes in porous silica matrices. In such examples the enzymes can function and have catalytic activity whilst in a porous silica matrix and this does not separate an enzyme from surrounding conditions.

A discontinuous silica coating or a porous silica matrix does not separate a virus or an enzyme from surrounding molecules and does not provide protection from denaturing conditions such as heat (100° C.) and/or acid pH and/or aging/long term storage or a combination of these such. Such advantages are provided by ensilication of the present invention.

A biomolecule enveloped with silica according to the present invention can have a substantially continuous silica envelope. The silica envelope separates the biomolecule from surrounding conditions. The silica envelope can be water impermeable.

The present invention uses a biomolecule as a template around which a silica envelope can grow. The silica envelope may not bond (or may not substantially bond) to the biomolecule. The silica envelope may not attach (or may not substantially attach) to the biomolecule. Therefore the present invention can be contrasted with silanisation in which silanes are deposited on a material surface, such as a mineral or inorganic surface offering —OH groups to form new —O—Si bonds.

Additionally the present invention can be contrasted with the sol-gel process. Sol-gel is a process of producing solid materials or coatings using polymerisation and condensation reactions of known oxides, such as silica ($SiO_2$) and titania ($TiO_2$). In sol-gel, production usually follows several well defined steps—conversion of monomers into a colloidal solution (sol), polymerisation or condensation reaction of monomers into gel, and then transformation into final product (aerogel, glass, thin film etc.). Major uses of sol-gel are in production of ceramics, coatings, thin films, support or entrapment of enzymes for catalysis, biosensors etc. Sol-gel processes are typically conducted at pH values away from neutrality, either acid or basic. Silica gels formed in this way are often microporous/nanoporous but their pores have random shapes.

The ensilication process is different from sol-gel in a number of aspects. Ensilication starts with monomers, as in sol-gel, but when added to a biomolecule solution, such as a protein solution, the monomers are forced to polymerise rapidly around the biomolecule itself, and precipitate. The gel is not produced, because it was found that if silica is allowed to gel, it grows into glass, which can damage the biomolecules. The ensilication reaction proceeds at close to neutral pH; this helps to ensure that the biomolecule is the nucleus for condensation. It has been found that a prolonged ensilication process tends to produce larger, harder particles, which resemble glass, and may be undesirable for some applications. Because the biomolecules used so far have been on the nanometer scale, the initially produced protein/silica particles have been on the nanometer scale too. These particles can grow and agglomerate further if the reaction is continued, due to the excess of silica in the solution. Buffer dilution may be used to halt this further growth.

The silica envelope can comprise covalently bonded amorphous silica deposited around the biomolecule. The silica envelope may comprise one or more layers of covalently bonded amorphous silica. The silica envelope may be amorphous nano-silica.

The silica envelope of the present invention can be formed from hydrolysed silica precursors deposited around the biomolecule. The silica envelope can be substantially continuous. The silica envelope can be formed around a single biomolecule.

Therefore the silica envelope of the present invention can be contrasted with some previous work involving silica and biological entities in which a virus or other entity is surface modified before a silica coating is applied, or in which silica nanoparticles are formed first and then applied to a virus or other entity or in which a silica gel or matrix is first formed and then contacted with enzymes.

The silica envelope prevents denaturation of the biomolecule. The silica envelope prevents unfolding, or loss of shape, or loss of structure of the biomolecule such as preventing loss of quaternary, or tertiary, or secondary structure. For protein biomolecules denaturation of the biomolecule can include unfolding of quaternary 4° structure involving several proteins folded together, can include unfolding of tertiary structure involving the folded shape, or can include unfolding of secondary structure such as an alpha helix or a beta sheets. The silica shell physically prevents the vaccine protein from denaturing (loss of shape and unfolding).

A biomolecule which can be enveloped with silica according to the present invention is a biological molecule with secondary or higher order structure important for its function. Therefore the biomolecule may have secondary structure, optionally the biomolecule has tertiary structure and further optionally the biomolecule has quaternary structure.

In the present invention a biomolecule can be a protein or a polypeptide. The protein or polypeptide can be a vaccine, a virus-like particle, an antibody or fragment thereof, or an enzyme.

Target vaccines which can be ensilicated for easier use, storage or transport include vaccines for measles, mumps, rubella, either individually or combined as MMR; tetanus, diphtheria, & acellular pertussis (DTP); Hepatitis B (HepB); Hepatitis A (HepA); Rotavirus (RV); Influenza ('flu vaccines) including *Haemophilus influenzae* type b (Hib); tetanus including the tetanus toxoid; meningitis including Meningococcal (Hib-MenCY; MenACWY-D; MenACWY-CRM); Meningococcal B; Human papillomavirus (such as 2vHPV:females only; 4vHPV, 9vHPV:males and females); Dengee vaccine, and Pneumococcal conjugate (PCV13).

Antibodies generally have to be frozen for storage, or for transport or both. Therefore antibodies and be can enveloped with silica according to the present invention. Reference to antibodies which may be enveloped with silica includes fragments of antibodies and immunoglobins. Fragments of antibodies may include single chain Fv antibodies (scFv), Fab fragments, F(ab')$_2$ fragments, Fc fragments, monospecific Fab$_2$, dispecific Fab$_2$, trispecific Fab$_3$, monovalent IgG, diabodies, bispecific diabodies, trispecific triabodies, scFv-Fv or minibodies.

In the present invention a biomolecule can be a carbohydrate or a polysaccharide. The carbohydrate to be enveloped with silica according to the present invention can be a carbohydrate vaccine or carbohydrate based vaccine, optionally the carbohydrate is a bacterial polysaccharide, such as a bacterial capsular polysaccharide, an example of which is pneumococcal polysaccharide vaccine (PPV).

In the present invention a biomolecule can be a therapeutic agent.

An individual biomolecule can be enveloped with silica to form a nanoparticle. Nanoparticles may agglomerate.

Another aspect of the present invention is a powder comprising a plurality of biomolecules enveloped with silica as described above. A powder of biomolecules enveloped with silica can be obtained by drying the product resulting from the method for enveloping biomolecules. Such a powder is suitable for transport and/or storage.

An additional aspect of the present invention is a suspension comprising a plurality of biomolecules enveloped with silica as described herein. A suspension of nanoparticles of biomolecules enveloped with silica may be obtained prior to nanoparticle aggregation. Such a suspension is suitable for transport and for storage.

A silica envelope of the present invention protects the biomolecule within it. The silica envelope can protect from harsh gastric conditions. The present invention provides an oral vaccine comprising a biomolecule enveloped with silica. The present invention also provides a gastric-resistant oral dosage form of a biomolecule, comprising the biomolecule enveloped with silica. Therefore a gastric resistant coating for a biomolecule can comprise a deposited layer of silica enveloping the biomolecule.

A biomolecule enveloped with silica can be for use in therapy. A biomolecule enveloped with silica can be for use in a method of vaccination. The described biomolecule enveloped with silica can be prepared as a pharmaceutically or physiologically acceptable preparation or composition containing a pharmaceutically or physiologically acceptable carrier, excipient or diluent. The pharmaceutically or physiologically acceptable preparation or composition can be administered to the tissues of the recipient organism of interest, including humans and non-human mammals.

A biomolecule released from its silica envelope, after transport and/or storage can be for use in a method vaccination. The biomolecule once released from its silica envelope can be prepared as a pharmaceutically or physiologically acceptable preparation or composition containing a pharmaceutically or physiologically acceptable carrier, excipient or diluent. The pharmaceutically or physiologically acceptable preparation or composition can be administered to the tissues of the recipient organism of interest, including humans and non-human mammals.

In another aspect the present invention provides a method of enveloping a biomolecule with silica. This may be achieved by addition of a silica-providing starting solution to a solution of biomolecules. The method can comprise:
  a) hydrolysing a silica starting material to produce a hydrolysed silica precursor,
  b) contacting the hydrolysed silica precursor with an aqueous solution comprising the biomolecule,
wherein the silica precursor precipitates about the biomolecule.

The method of enveloping a biomolecule with silica preferably occurs in aqueous phase.

A silica starting material contains silicon atoms coordinated by labile organic groups. The silicon atoms can be coordinated by alkoxide groups or derivatives of alkoxide groups. A silica starting material can comprise alkoxysilane. Therefore the silicon atoms can be coordinated by methoxy, ethoxy, propyoxy, butoxy, pentoxy, hexaoxy groups or derivatives thereof. Examples of silica starting materials include tetra-methoxy-orthosilicate (TMOS), tetra-ethoxy-orthosilicate (TEOS), tetra-propoxy-orthosilicate (TPOS), tetra-butoxy-orthosilicate (TBOS), and tetra (ethoxymethoxy) silane. A preferred silica starting material is or comprises TEOS.

The silica starting material is hydrolysed before contacting with the biomolecule. Therefore this step can be referred to herein as pre-hydrolysis. Hydrolysing a silica starting material produces a hydrolysed silica precursor. Hydrolysing a silica starting material is performed at acidic pH. The acidic pH can be less than or equal to 4.5, 3.5, 3.0, 2.5 or 2.0. In some methods the step of hydrolysing a silica starting material (the pre-hydrolysis step) is performed at pH 3.0 or below, or at about pH 2.0. A preferred acidifying agent is HCl.

The hydrolysed silica precursor can comprise silica monomers. The silica monomers can include $SiO_2$, or $^-O$-$Si$-$O^-$. It is understood that $SiO_2$ may be a bulk formula. At the microscopic level each silicon atom is generally coordinated by four oxygen atoms and the hydrolysed silica precursor can be tetrahedrally coordinated silica, such as $Si(OH)_4$ or $$^-O-\underset{\underset{O^-}{|}}{\overset{\overset{O^-}{|}}{Si}}-O^-$$

The hydrolysed silica precursor can comprise hydrolysed alkoxysilane, and preferably comprises hydrolysed TEOS.

The hydrolysed silica precursor is contacted with the biomolecule to precipitate or grow the silica envelope around the biomolecule. Forming a silica envelope is a modified sol-gel process in which a silica gel is prevented from forming. Instead silica goes from the hydrolysed silica precursor to precipitation of the silica around the biomolecule. In the absence of a biomolecule as a template this silica would go to gel and then to glass if left for long enough. Once hydrolysed silica precursor and biomolecule are contacted, silica grows a network and rapidly precipitates. The precipitant is in a nanoform, making it nano-silica, which has formed around the biomolecule.

An aqueous solution of the silica starting material appears to form two phases, whereas the hydrolysed silica precursor can appear as a single phase. The hydrolysed silica precursor can appear homogeneous. The hydrolysed silica precursor can appear to have viscosity similar to water. The present inventors advantageously selected hydrolysed silica precursor to contact with an aqueous solution comprising the biomolecule.

Hydrolysing a silica starting material is performed until the silica atoms of the silica starting material are substantially no longer coordinated by labile organic groups. The hydrolysed silica precursor is advantageously contacted with an aqueous solution comprising the biomolecule before the reaction progresses such that silica forms longer chains of silica.

Formation of longer chains of silica may give the solution of hydrolysed silica starting material a viscosity appearing greater than that of water. Formation of longer chains of silica or increasing viscosity can be an indication that nanoparticles or a porous gel are forming. Consequently, the methods of ensilication of the present invention use hydrolysed silica precursor at a different stage of preparation from some previous work which contacted nanoparticles or porous gels of silica with viruses or enzymes. Optionally a visual test can confirm the hydrolysed silica precursor forms a single phase in aqueous solution and has a viscosity similar to water.

The aqueous solution comprising the biomolecule further comprises a buffer and can have a $pH \geq 6$. The aqueous solution comprising the biomolecule and the buffer can have a pH in the range of $6.5 \leq pH \geq 7.5$. A preferred pH for the aqueous solution comprising the biomolecule and the buffer is about 7. The buffer in the aqueous solution comprising the biomolecule can be Tris-HCl. The buffer in the aqueous solution comprising the biomolecule can be at a concentration greater than 10 mM, 15 mM, 20 mM or 25 mM or 30 mM.

The aqueous solution comprising the biomolecule can have the biomolecule at a concentration less than that which causes spontaneous aggregation of the biomolecule. The concentration of a biomolecule at which spontaneous aggregation may occur is dependent on the biomolecule and on the conditions. A person skilled in the art can determine the concentration below which to perform the present invention. For example, the aqueous solution comprising the biomolecule can have the biomolecule at a concentration of less than or equal to 5 mg/ml, 4 mg/ml, 3 mg/ml, or 2 mg/ml or 1.5 mg/ml, or 1 mg/ml.

Contacting the hydrolysed silica precursor with an aqueous solution comprising the biomolecule can occur at a $pH \geq 6$. Contacting the hydrolysed silica precursor with an aqueous solution comprising the biomolecule can occur at a pH in the range of $6.5 \leq pH \geq 7.5$. In a preferred embodiment the pH can be about 7. Therefore the ensilication process occurs at, or about neutral pH, such as in the range of $6.0 \leq pH \leq 8.0$, optionally $6.5 \leq pH \leq 7.5$, or about pH 7.

The hydrolysed silica precursor is understood to rapidly polymerise and/or precipitate around the biomolecule. Contacting the hydrolysed silica precursor with biomolecule can be for less than 20 minutes, less than 15 minutes, less than 10 minutes, less than 5, 4, 3, 2 or 1 minute, or less than 50 seconds, less than 40 seconds, less than 30 seconds, less than 20 seconds, less than 10 seconds. The biomolecule may become coated with silica in only 1, 2, 3 or a few seconds. Shorter times for contacting the hydrolysed silica precursor with biomolecule will form individual nanoparticles. A nanoparticle comprising a biomolecule enveloped with silica. Longer times for contacting the hydrolysed silica precursor with biomolecule will allow for nanoparticle agglomeration.

On contacting the hydrolysed silica precursor with an aqueous solution comprising the biomolecule, the silica precursor precipitates about the biomolecule to form covalently bonded amorphous silica about the biomolecule.

Contacting the hydrolysed silica precursor with an aqueous solution comprising the biomolecule preferably precipitates a silica envelope about a single biomolecule. Advantageously the silica envelope formed by the method of the present invention is substantially continuous and separates the biomolecule from surrounding conditions, including denaturing conditions and molecules or cells with which the biomolecule might react.

The present invention also provides a method of reducing biomolecule denaturation in non-physiological conditions comprising enveloping the biomolecule with silica, the enveloping comprising contacting a hydrolysed silica precursor with an aqueous solution comprising the biomolecule as described herein so that the silica precursor precipitates about the biomolecule.

Figure 2A:
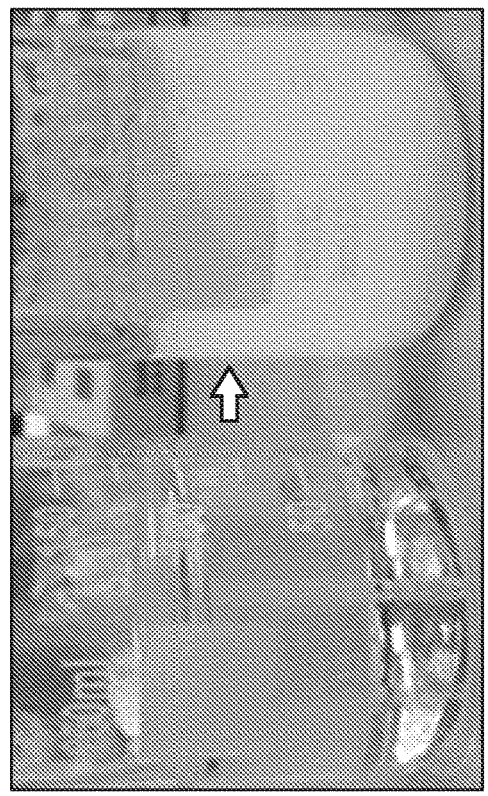

Ensilicated biomolecules do not need to be kept under refrigerated conditions since they are protected by the silica envelope. The present invention also provides a method of transporting and/or storing a biomolecule, comprising i) obtaining the biomolecule enveloped with silica ii) transporting the biomolecule from a first location to a second location and/or storing the biomolecule, wherein at least a portion of the transporting and/or storing occurs in the absence of a cold-chain. The method may also comprise contacting hydrolysed silica precursor with an aqueous solution comprising the biomolecule so that silica precipitates about the biomolecule. Reducing or removing reliance on cold-chain reduces the cost transport and storage of biomolecules.

A further aspect of the present invention is a method of providing a gastric resistant coating to a biomolecule comprising contacting a hydrolysed silica precursor with an aqueous solution comprising the biomolecule, wherein the silica precursor precipitates about the biomolecule agent to form the gastric resistant coat. The biomolecule can be a therapeutic agent and may be as described herein.

The present invention also embraces a method of vaccination comprising administering to a subject in need thereof, a vaccine comprising a biomolecule enveloped with silica. The envelope can comprise covalently bonded amorphous silica deposited around the biomolecule. The biomolecule can be a therapeutic agent and may be as described herein. Administration of the vaccine can be oral administration. The present invention further embraces a method of vaccination comprising administration to a subject in need thereof, a biomolecule with secondary or higher order structure, by oral administration of the biomolecule enveloped with silica.

Some biomolecules require administration by routes other than oral administration, for example by injection. Therefore the biomolecule may be released from its silica envelope prior to administration. The present invention further embraces a method of vaccination comprising administration to a subject in need thereof, of a biomolecule with secondary or higher order structure, wherein the method includes release of the biomolecule from a silica envelope followed by re-formulation of the biomolecule and injection into the subject.

Consequently, a further aspect of the present invention provides a method for releasing a biomolecule from an envelope of silica deposited around the biomolecule, comprising contacting the biomolecule and its envelope of silica with a release solution comprising fluoride ions at acidic pH. The release solution comprises buffer, fluoride ions (for example from NaF) and is adjusted to acidic pH (for example with HCL). It has been identified that acidic conditions alone do not allow release of the biomolecule, and fluoride ions alone do not allow release of the biomolecule. The method may further comprise agitation of the mixture. The release stage of contacting the biomolecule and its envelope of silica with a release solution comprising fluoride ions at acidic pH, optionally with agitation, may be from about 10 minutes to about 2 hours, about 30 minutes to about 90 minutes, or about an hour. Biomolecules enveloped with silica may be in powder form when contacted with release solution.

Sufficient fluoride ions are required to achieve good release of biomolecule. The release solution can comprise a fluoride ion concentration of from about 75 mM to about 150 mM, optionally the fluoride ion concentration is from about 75 mM to about 125 mM, further optionally the fluoride ion concentration is from about 85 mM to about 115 mM. Removal of any excess fluoride ions can be achieved by addition of a salt, such as a calcium salt, leading to precipitation of a fluoride salt such as calcium fluoride. Removal of excess fluoride ions may be performed following the release stage, such as immediately following the release stage.

An acidic pH is required to achieve good release of biomolecule. The release solution can have a pH less than or equal to 6.0 but greater than 3.0, optionally greater than or equal to 4.0. The release solution can have a pH of less than or equal to 6.0, preferably is less than or equal to 5.5, or is less than or equal to 5.0, or is less than or equal to 4.5, or is less than or equal to 4.0, or is less than or equal to 3.5. Generally the pH of the release solution is not less than 3.0. The pH of the release solution can be adjusted to about pH 5.0 or about 4.5 or about 4.0.

The release solution comprises buffer which can protect released biomolecule.

The pH of the release solution can be equal to or above 4.0 or 4.5.

In embodiments the present invention provides a method incorporating ensilication and subsequent release of a biomolecule. Such a method comprises hydrolysing a silica starting material to produce an aqueous solution of hydrolysed silica precursor, contacting the hydrolysed silica precursor with an aqueous solution comprising the biomolecule wherein the silica precursor precipitates about the biomolecule, and contacting the biomolecule and its silica envelope with a release solution comprising fluoride ions at acidic pH.

The release stage can be temporally or spatially separated from the ensilication stage by, for example storage or transport.

Further features of the ensilication and release are as described above.

EXAMPLES

Example 1—Ensilication and Release of Lysozyme and Haemoglobin

To test the ensilication and release process we used hen egg white lysozyme, a robust and well-characterised protein with enzymatic activity, and horse haemoglobin, a heterotetrameric protein with a complex tertiary and quaternary structure and therefore more susceptible to denaturation. It should be noted that these methods could be applied to ensilicate any biomolecule as described herein.

We have subjected ensilicated proteins to heating at 100° C. under dry and wet conditions, and aging for up to six months at room temperature. We have then released proteins from ensilication, using an acidic fluoride solution, to assess the preservation of structure and function. Our results indicate that ensilicated proteins can survive conditions such as intense heat treatment, which otherwise denature the unprotected protein in solution, and can then be released intact into solution.

The ensilication and release process is shown schematically in FIG. 1B and described in more detail below. A solution of silica precursor materials (pre-hydrolysed tetraethyl-orthosilicate (TEOS)) is added to the protein solution, and stirred for 20 minutes. Precipitates similar to sol-gel are rapidly formed, as shown in FIG. 2A, and later vacuum filtered. Ensilicated proteins retained on the filter are washed with MilliQ water and methanol in order to remove any free protein that is not ensilicated and is left on the surface. Collected ensilicated powders are left to dry in an extractor for 24 hours, and then weighed.

Figure 2B:
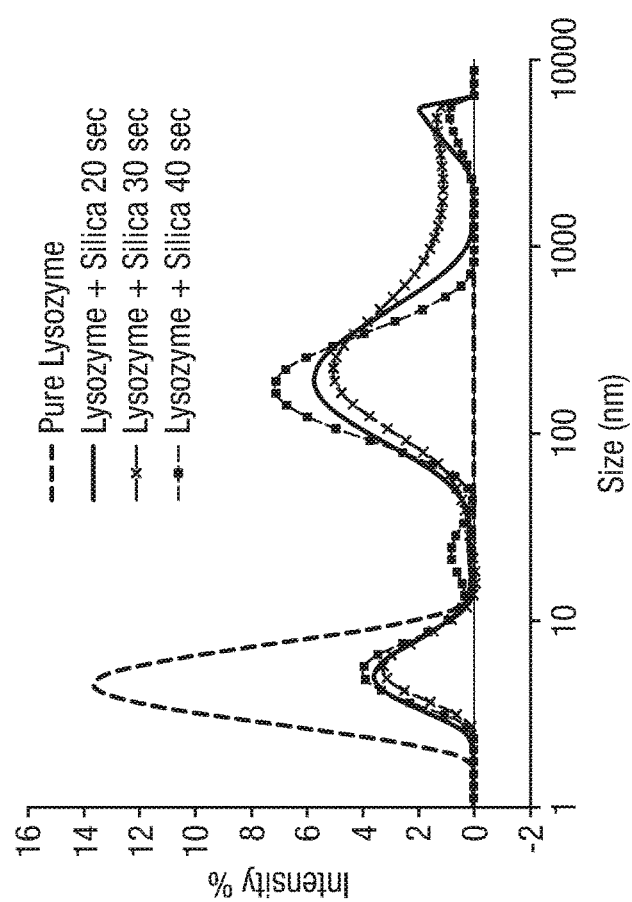
Figure 2C:
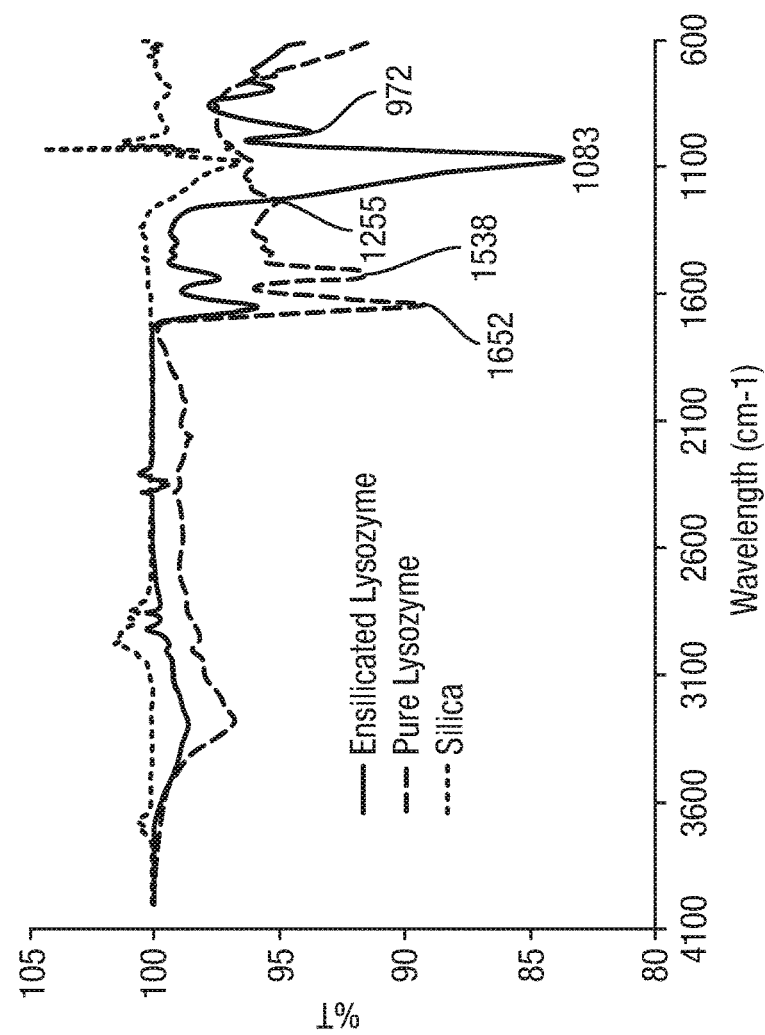
Figure 2D:
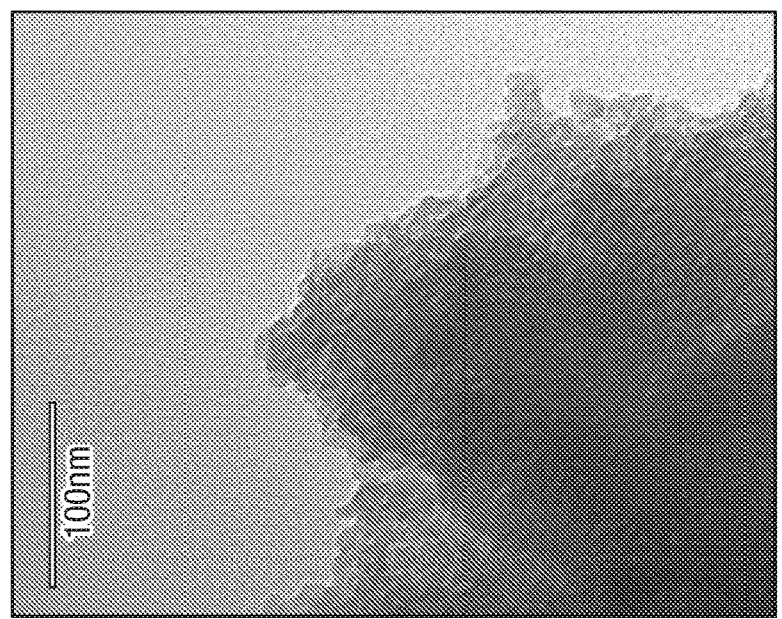

Ensilication of 100 mg of lysozyme produces on average 182.68±7.18 mg of powder. The ensilicated material forms and precipitates rapidly. We were, however, able to obtain some Dynamic Light Scattering (DLS) data on particle size during the process, as shown in FIG. 2B. An initial solution of lysozyme shows peaks corresponding to particles 4 nm in diameter, which correspond to individual lysozyme molecules. After the addition of silica, a signal corresponding to larger particles with diameters around 200 nm appears within tens of seconds, showing that silica precipitation on the protein occurs immediately after the addition. We attribute this signal to the aggregation of silica nanoparticles nucleated on the protein molecules. Further analysis of the ensilicated material by transmission electron microscopy (TEM), after a more prolonged ensilication treatment (5 hours stirring after addition of TEOS), confirmed the presence of aggregated silica nanoparticles (FIG. 2C). Fourier Transform Infrared Spectroscopy (FT-IR) spectra for native lysozyme, silica and the ensilicated material are presented in FIG. 2D. We observe both amide peaks from lysozyme and silica vibrational bands, showing that the protein and silica exist together in the precipitated material. Assessment of the residual lysozyme protein concentration in the supernatant after the sol-gel precipitates formation indicates that more than 95% of the lysozyme initially present is successfully ensilicated.

Silica is specifically vulnerable to attack by acidic fluoride solutions. We therefore use a release protocol involving treatment with a dilute solution of sodium fluoride, acidified to pH 4.0 using HCl (described in more detail below), to release the entrapped proteins into solution from samples of ensilicated materials. After release, protein levels of lysozyme were measured and showed that release efficiency was on the order of 95%. Treatment using either fluoride or acid separately did not dissolve the silica or release proteins. Experiments monitoring the release of ensilicated lysozyme at different pH values (pH 7.0 to 3.0) demonstrated that a pH of 4.0 or lower in combination with sodium fluoride was necessary for efficient release of the proteins (data not shown). For this study, the purpose of the release protocol was to establish that release of intact protein was possible. Since fluoride in solution is toxic at high concentrations, causing gastrointestinal distress at a dose of around 100-150 mg, biological applications may require investigation of alternative release methods, or the removal of fluoride by conversion to insoluble $CaF_2$ with the addition of a solution of calcium salts.

Figure 6:
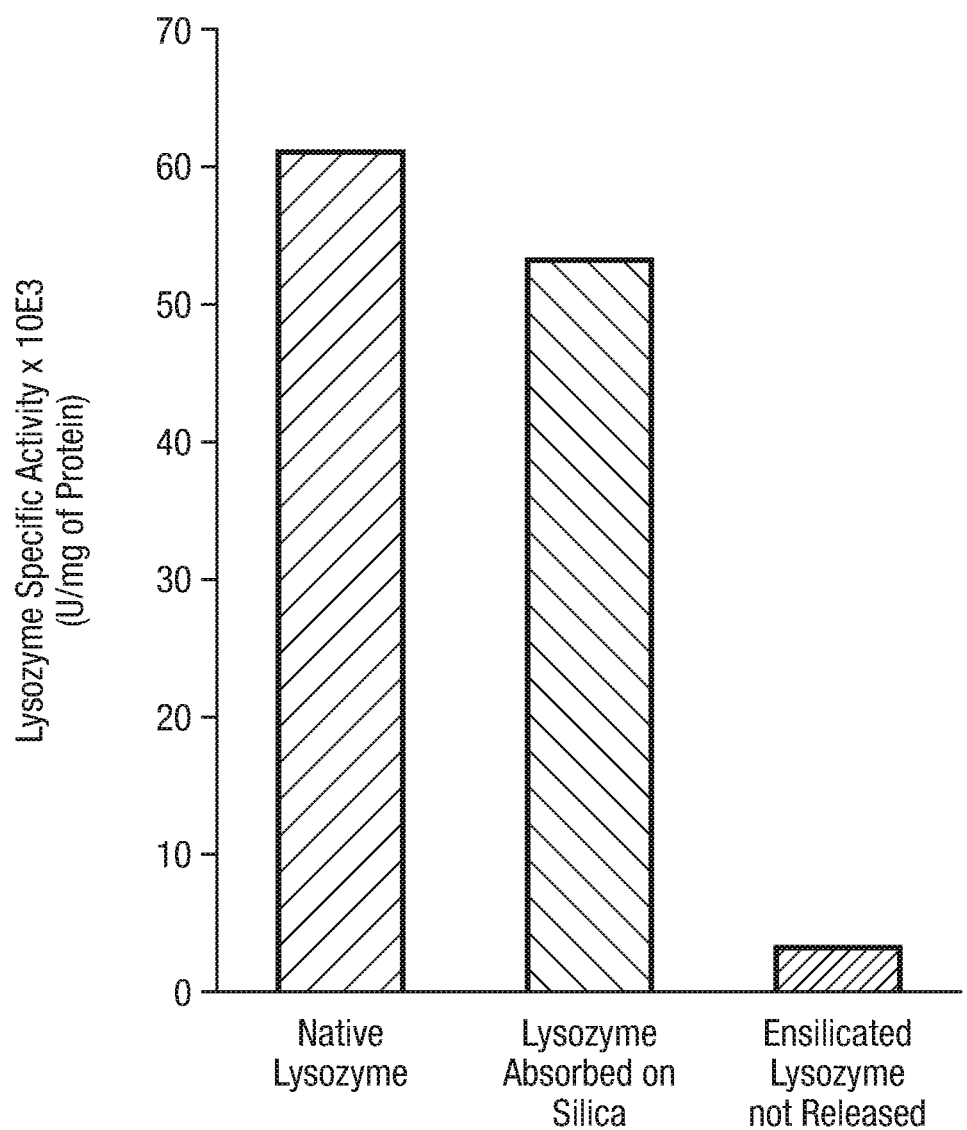

Mass spectrometry analysis on lysozyme before and after ensilication detected a single peak at 14305 Daltons (see FIG. 4), indicating that the protein chain remains intact during ensilication and release. Using EnzCheck lysozyme assay kit we compared the specific activity of the released protein from ensilicated samples to that of the starting material, and thus assess the level of protection provided by the ensilication procedure. Lysozyme activity assays were performed on the ensilicated and released material following various treatment regimes (FIG. 3A). A high proportion (95%) of lysozyme released from ensilication remains functional and intact, and even after heating at 100° C. for 5 h at least 75% of the enzymatic activity is retained (FIG. 3A). Native lysozyme heated to 100° C. in aqueous solution, by contrast, is denatured and loses function as expected. The ensilicated lysozyme is protected from attacks form chemical agents, as treatment with 10 N HCl did not alter the specific activity of the enzyme. Non-released lysozyme, still trapped in silica, had no detectable enzyme activity, testifying that the lysozyme is well encapsulated within the silica and inaccessible for its substrate (FIG. 6). We also measured the enzymatic activity of lysozyme that was absorbed onto a layer of silica (described in further detail below). Under this condition, a very small amount of lysozyme is adsorbed in the silica matrix and the enzyme is almost fully accessible to the substrate, as the measured specific enzyme activity was similar to the activity of the native lysozyme (FIG. 6).

Circular dichroism (CD) analysis confirmed that the ensilicated lysozyme displays the same CD signal as the starting materials, while the unprotected protein subjected to heat treatment shows dramatic changes in the CD signal, indicating loss of secondary structure (FIG. 3B).

The structural integrity of the ensilicated lysozyme was analysed by SDS-polyacrylamide gel electrophoresis (FIG. 3C). The native lysozyme heated in solution displays alterations of the structural integrity of the protein (FIG. 3C, lane 7), with the presence of both lower molecular weight protein fragments and higher molecular weight complexes (a lysozyme dimer band is visible at approx. 27 kDa). The ensilicated and released protein, by contrast, appears identical to the starting material and so appears to be structurally intact.

We confirmed that the ensilication and release procedure doesn't affect the secondary and tertiary structure of lysozyme by resolving the crystal structure of the ensilicated and released lysozyme. The ensilicated and released lysozyme structure showed a 100% overlap with already published structures of native lysozyme (FIG. 3D).

Figure 4A:
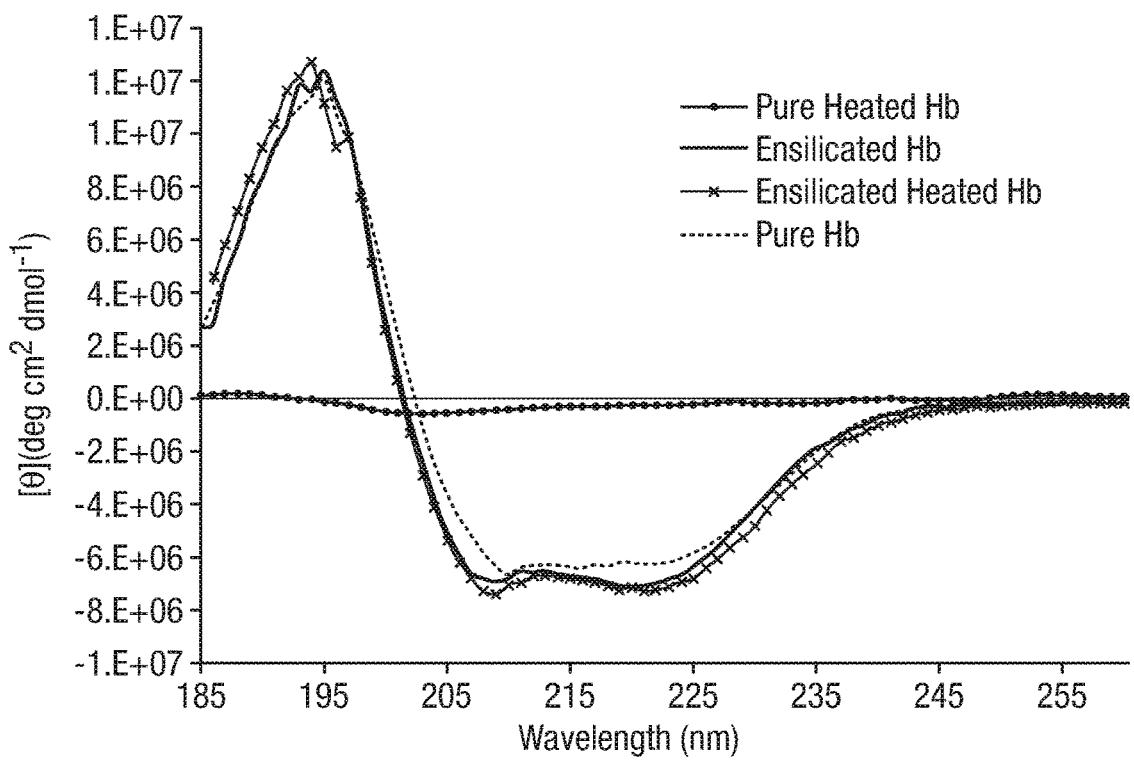
Figure 4B:
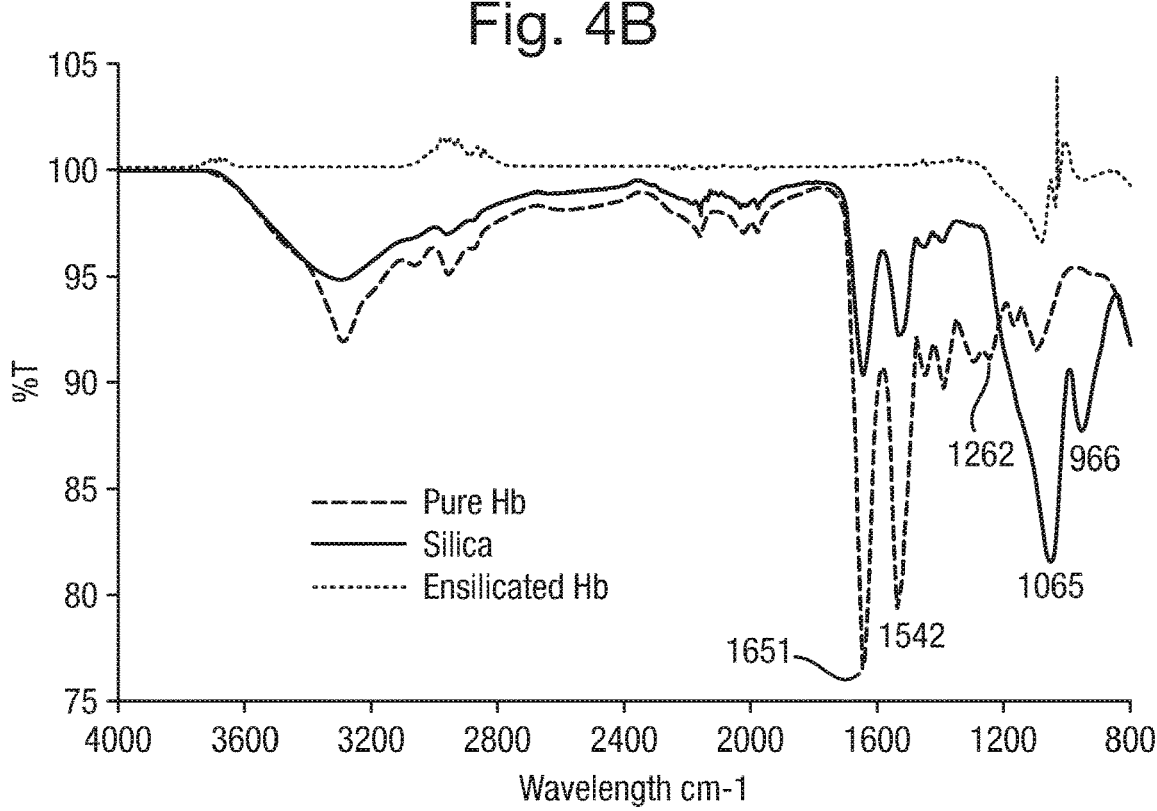
Figure 5A:
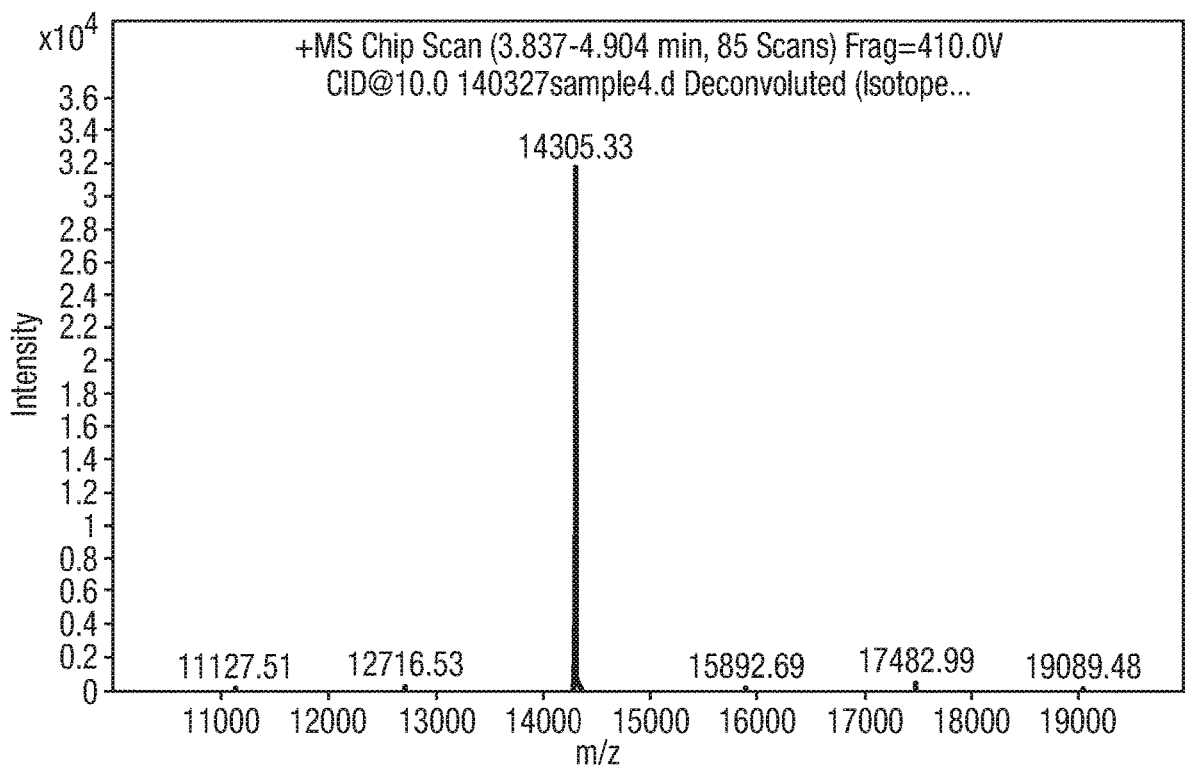
Figure 5B:
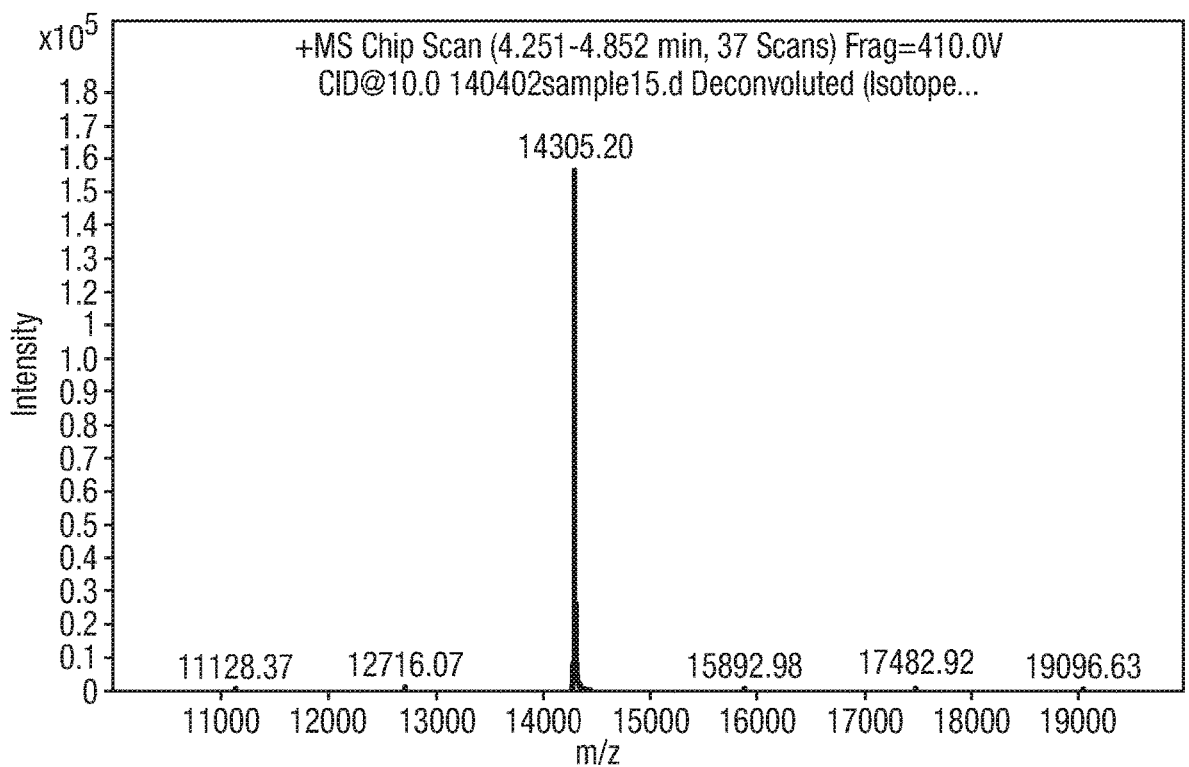

Having established that ensilication, preservation and release are possible for lysozyme, we have also applied our protocol to horse haemoglobin (Hb). Ensilication of 100 mg Hb produced on average 87.43±4 mg of ensilicated powder, indicating a lower efficiency of ensilication. By contrast to lysozyme, Hb protein determination on the supernatant after ensilication confirmed that more Hb remained in solution and that only 46% of the Hb was ensilicated. The FT-IR analysis of the ensilicated material confirmed the presence of silica and Hb (FIG. 4A). Overall, the ensilication efficiency for Hb was about 3 times lower than for lysozyme, probably due to the difference in size and charge of the overall protein. This suggests that the ensilication protocol will in general have to be adjusted for different materials. However, ensilication does appear effective in preserving the ensilicated Hb from heat denaturation. CD analysis confirmed that the protein's secondary structure is preserved through ensilication, heat treatment and release, whereas heat-treated Hb without protection displays an obvious and dramatic loss of structure (FIG. 4B).

Our results demonstrate for the first time that proteins in solution can be fully encased in a covalently bonded silica network and subsequently released back into solution, intact and functional. The ensilicated protein survives heat treatment that is capable of denaturing proteins in solution, indicating that the silica is effective in maintaining protein structure, physically preventing its unfolding and denaturation. The process can produce a suspension of silica nanoparticles enveloping individual proteins. The process can also produce a solid (particulate) protein-loaded product directly from solution. The process may thus be suitable for use with proteins that do not tolerate lyophilisation (freeze-drying). Treatment with mild acid and fluoride is effective in releasing intact, functional proteins from ensilication.

Ensilication Protocol

500:500:1 of Mili-Q water, TEOS and 32% HCl were stirred for 1 hour at 20° C. for TEOS pre-hydrolysation. Lysozyme or hemoglobin solution was prepared as a 100 ml mixture of 1 mg/ml protein in 50 mM Tris-HCl pH 7, stirred using a 25×8 mm octagonal magnetic stir bar (Fisher Scientific) at 60 rpm in a 250 ml beaker for 0.5 h at 20° C. The pre-hydrolysed TEOS is then added to the protein solution with a ratio of 1:50, and stirred at 125 rpm for 20 min. After 20 min, the mixture is vacuum filtered using a Microfibre Filter MF 300 with 0.7 µm retention (Fisher Scientific). Once supernatants filtered from the protein ensilication are collected, gels are washed with MilliQ water and methanol thoroughly in order to remove any non-ensilicated protein left on the surface. Collected ensilicated protein powders are left to dry in an extractor for 24 h, and then weighed.

As an alternative ensilication protocol, the pre-hydrolysed TEOS is added to the protein solution and stirred for only a few seconds, for example 1-10 seconds. At this stage the reaction can be quenched by addition of lower pH buffer to prevent silica particle aggregation. The resulting product is a suspension of silica nanoparticles.

A control experiment using lysozyme absorbed onto silica was also performed. For this 100 mg silica (SIGMA-Aldrich, Davisil, Grade 646, pore size 150 Å, 35-60 mesh) was soaked with 100 ml 1 mg/ml lysozyme in 50 mM Tris-HCl pH 7.0, for 20 min at 20° C. The lysozyme-solution-bathed silica was then vacuum filtered and left to dry overnight in the fume hood. The supernatant from the filtration was collected.

Treatment Protocols—Heat, Acid and Aging

To test whether the ensilication protects against intense heat, ensilicated powders were heated at 100° C. between 3 and 5 h. The pure lysozyme and Hb proteins were solubilized in 50 mM Tris-HCl pH 7.0 at a final concentration of 1 mg/ml and heated at 100° C. for the same length of time. To test the resistance to acid the powdered ensilicated lysozyme was incubated for 3 h in 10 M HCl. The powdered ensilicated lysozyme samples were stored at 22° C. for 6 months to test stability against aging.

Release Protocol

To release protein from silica, 5 ml of 50 mM Tris-HCl pH 7.0 and 5 ml release buffer (190 mM NaF in Milli-Q water and adjusted to pH 4.0 with HCl) together referred to as the release buffer are mixed with 5 mg of ensilicated protein powder in a tube rotator at 20° C. for 1 h.

Protein Concentration Assay

The protein concentration was measured using BCA protein assay kit (Thermo Fisher) according the manufacturer's instructions.

Dynamic Light Scattering (DLS)

Malvern Zetasizer Nano ZS was used to measure the hydrodynamic size by dynamic light scattering (DLS) for both lysozyme and to follow the process of lysozyme ensilication with a count rate of 228.8 kcps, measurement position 3 mm, attenuator 11 and duration 60 seconds at 25° C. To monitor the onset of the ensilication process, we used DLS to measure particle size before (0 sec) and immediately after adding 4 µl pre-hydrolysed TEOS to 200 µl 1 mg/ml lysozyme solution at every 20, 30 and 40 seconds.

Lysozyme Activity Assay

We used EnzChek® Lysozyme Assay Kit from Life Technology following the manufacturer's instructions.

Crystallisation, X-ray Diffraction Data Collection and 3D Structure Determination of Released Lysozyme Crystallisation of lysozyme released from silica was achieved with use of the hanging drop vapour diffusion technique[19]. Released lysozyme at a concentration of 25 mg/ml in 0.1 M sodium acetate pH 4.6[20] was crystallised in 1.5 M NaCl in 0.1 M sodium acetate pH 4.6[21]. Crystals suitable for X-ray diffraction analysis formed after approximately 5 days incubation at 18° C.

Crystals were flash frozen in a loop (reservoir solution +25% glycerol) under a continuous nitrogen cryo stream (Oxford Cryosystems Cobra) and full data set was collected on an in-house rotating anode X-ray source (Rigaku Micro-Max-007HF) with a Saturn 944+ CCD detector (see Sup. Table S1 for data collection statistics). The structure of released lysozyme was resolved using molecular replacement (using Balbes) and refined (using Phenix) with model building in COOT (see Sup. Table S2 for refinement statistics).

Transmission Electron Microscopy (TEM)

For TEM, ensilicated lysozyme powder was thinly coated on a Cu grid, dried under low vacuum to remove any unwanted solvents, and left under low vacuum overnight. For analyses a Jeol 1200 EXII microscope with Gatan Dual View Camera and a Thermo Ultra Dry EDS detector with Noran 7 were used, with the microscope operated at 120 kV and with a magnification of $250 \times 10^3$.

Fourier Transform Infrared Spectroscopy (FT-IR)

FT-IR spectra between wavelength 4000 $cm^{-1}$ land 600 $cm^{-1}$ were accumulated from 25 scans with a resolution of 2 $cm^{-1}$, data interval of 0.5 $cm^{-1}$ and a scan speed at 0.2 cm/s on a Perkin Elmer Frontier FTIR spectroscope.

Circular Dichroism

Synchrotron radiation circular dichroism spectra for lysozyme were collected at the Diamond Light Source, Didcot, on beamline B23 over a wavelength range of 180 to 260 nm with an integration time of 2 s and a data interval of 1 nm. For haemoglobin, a Chirascan™ CD Spectrometer (Applied Photophysics) was used with the same parameters as at the synchrotron. Proteins were dialysed into 100 mM sodium phosphate buffer pH 7.0 and protein concentration was adjusted to 0.1 mg/mL. The samples were run in 0.5 mm quartz cuvettes at 20° C.

SDS-Polyacrylamide Gel Electrophoresis (SDS-PAGE)

Protein samples were prepared in SDS-sample buffer and loaded on a 15% tris-glycine SDS-polyacrylamide gel. Protein bands were visualised with Coomassie Blue stain.

Mass Spectrometry

NanoLC coupled to Electrospray Quadrupole Time-of-Flight (ESI-QTOF, Bruker, Karlsruhe, Germany) was applied to identify the biomaterial before and after ensilication.

Statistical Analysis

When indicated, results were analysed using two tailed un-paired t-tests. p values<0.05 were considered statistically different.

Crystallisation of Released Lysozyme

Crystallisation of lysozyme released from silica was achieved with use of the 'hanging drop' vapour diffusion technique. Pure lysozyme has been crystallised on many occasions before and the conditions mentioned here have been adapted from literature for use within this procedure. Released lysozyme was dialysed in 0.1 M sodium acetate pH 4.6 and concentrated to 25 mg/ml. In a 24-wells crystallisation plate, 700 µl of 1.5 M NaCl in 0.1 M sodium acetate pH 4.6 was added to each reservoir. The lysozyme solution was mixed 1:1 on a siliconized coverslip with reservoir solution creating a 2 µl droplet. Diffusion within the covered well provided changes in the precipitant causing the reservoir solution to retain more water, thus providing the formation of crystals within the droplet as the protein concentration increased, until equilibrium was obtained. Crystals were formed after approximately 5 days incubation at 18° C.

Example 2: Simplified Lysozyme and Tetanus Toxoid Ensilication and Release Protocols 1. Preparation of 50 mM Tris-HCL in MilliQ pH 7.0 (0.5 L)
   Use plastic container or large beaker with magnetic stirrer
   Weigh out 3.03 gr of Trizma base (MW 121.14 g/mol, Cat:T666-1KG, Sigma)
   Add weighed powder to 400 ml MilliQ and stir
   Check pH and use HCL (Hydrochloric acid, 32%) to lower the pH until it stabilises at 7
   Put empty bottle on scale and set to zero
   Fill up bottle with solution and top up to 500 ml (=500 gr)
2. Preparation of TEOS:$H_2O$:HCL Solution, 1:1:0.02 Ratio
   Use a 100 ml glass beaker with a magnetic stirrer
   Measure 20 ml of TEOS (Tetraethyl Orthosillicate, Cat: 86578-1L Sigma) and add to 100 ml glass beaker
   Measure 20 ml of MilliQ $H_2O$ and add to beaker containing TEOS
   Add 40 µl HCL (Hydrochloric acid, 32%, Cat: Sigma)
   Place on stirrer at 350 rpm, check every 30 minutes until mixture has become homogenous
   Mixture can be used after 20 minutes of becoming 1 phase (pre-hydrolysed solution)
3. Prepare Lysozyme Solution
   Weigh out 100 mg of lysozyme (from chicken egg white, Cat: 62971-10g-F, Sigma)
   Add lysozyme to 100 ml of Tris-HCL pH 7 buffer in 250 ml glass beaker with magnetic stirrer
   Mix without forming air bubbles
   Set mixture at 60 rpm stirring speed
4. Lysozyme Ensilication OR (See Below)
   Add 2 ml of the pre-hydrolyse to the 100 mg/100 ml (1 mg/ml) lysozyme solution
   Incubate until solution becomes turbid for max 20 min
   Prepare filter setup:
      Ceramic filter funnel, glass microfiber paper MF300, 55 mm, 0.7 µm size
      Glass Erlenmeyer with vacuum tube opening
      Vacuum machine
   Filter the solution by pulling vacuum through the Erlenmeyer
   Washed filter residue with MilliQ
   Leave ON to dry, weigh and collect ensillicated material
5. TTCF Ensilication
   Purified solution of tetanus toxoid C fragment (TTCF) at 1 mg/ml ranging in volumes 5-25 ml (depending on yield of culture)
   Add in a 1:50 ratio pre-hydrolysed TEOS
   Incubate until solution becomes turbid for max 20 min
   Prepare filter setup:
      Ceramic filter funnel, glass microfiber paper MF300, 55 mm, 0.7 µm size
      Glass Erlenmeyer with vacuum tube opening
      Vacuum machine
   Filter the solution by pulling vacuum through the Erlenmeyer
   Washed filter residue with MilliQ 4×10 ml, collect supernatant and washes for testing
   Leave ON to dry, weigh and collect ensillicated material
6. Preparation of NaF+HCL→Na+F−Buffer (8 mg/ml)
   Weigh out 1600 mg of sodium fluoride (cat: 21154 sigma)
   Add to 200 ml of MilliQ
   Add HCL to solution until pH 4.0
   Store in fridge in plastic container
7. Release Ensilicated Material
   Weigh out 5 mg of ensilicated material in 15 ml tube
   Add 5 ml 50 mM Tris-HCL pH 7
   Add 5 ml NaF buffer
   Incubated 1 hr at RT, rotating It will be noted that this protocol can be adapted for ensilication and release of any biomolecule as described herein

Example 3—Ensilication and Release of Tetanus Toxoid

Our research group has assessed the following objectives to qualify this method suitable for storage and transport of vaccines: 1) silica matrix formation incorporating the TTCF protein. 2) subsequent release of TTCF from silica. 3) analysis of released TTCF from silica to confirm preservation of structural integrity and function.

Purified Histidine Tagged rTTCF pET-16b His-tag rTTCF plasmid, developed by Dr A. Knight, was kindly provided by Dr K. Marchbank. Using a heat-shock treatment on a vial of thawed BL21(DE3) (Novagen, UK), transfection was assessed after an overnight culture on a Luria Broth (LB) agar plate containing ampicillin. Transfected E. coli was cultured in LB medium at 37° C., 200 rpm. Isopropyl β-D-1-thiogalactopyranoside (IPTG) was used to initiate the 52 kDa TTCF protein production.

Bacterial culture was incubated for approx. 5 hours and pellets harvested were stored at −80° C. Using a (Åkta) HisTrap™ column, the rTTCF was bound onto the column followed by gradient elution and collected from pooled fractions to be dialysed against neutral Tris buffer. Pierce™ BCA (Thermo Scientific, UK) analysis was performed to determine yield of purified TTCF in mg/ml.

Silica Matrix Formation

A solution of pre-hydrolysed TEOS was prepared to be added to TTCF protein in solution. Polymerisation occurred under specific conditions which were time gated. Once the silica matrix formation was completed, the solution was filtered and dry powder was collected after 48 hours at room temperature.

Release of rTTCF from Silica

Na—F release buffer was prepared at 190 mM in $ddH_2O$ and acidified with hydrochloric acid (32%). 5 mg of TTCF powder was weighed and added to a 15 ml tube. 5 ml of neutral buffer was added to this tube followed by the addition of 5 ml of release buffer. The tube was placed on a rotator for 1 hour at RT. The released protein was then kept at 4° C. and analysed for structural and functional analysis.

SDS-PAGE

Molecular weight analysis on native and released TTCF sample was carried out by SDS-PAGE gel-electrophoresis. Samples were run over a 10% linear slab SDS gel using a Mini-Protean3 (Bio-Rad) SDS-PAGE system. Sample and pre-stained ladder (Novex Sharp, Thermo Scientific, UK) were added and the gel was run for 45 min at 200V. Visualisation of sample bands was done using 15-25 ml PageBlue staining overnight at room temperature (RT).

Western Blot

Confirming histidine residue of native and released TTCF protein was done using Western Blot. SDS-PAGE gel was placed in a semi-dry blotting machine and a current was run at 0.8 $mA/cm^2$ to transfer proteins from gel to nitrocellulose membrane, followed by incubation in TBS-Tween with 5% casein for 35 minutes at RT. An anti-histidine IgG conjugated with horseradish peroxidase (HRP) antibody was added and incubated for 1 hour at RT. After several washes in TBST, a luminol substrate mixture was added to the membrane followed by luminescent imaging.

UV-Vis

UV-visible absorbance spectra for analysis of protein absorbance was performed on aqueous samples using a Perkin Elmer Lambda 650 S spectrometer. Range of absorbance analysed was 320-200 nm and samples were prepared to even out protein concentrations and were blanked to their according buffers.

Circular Dichroism

Protein chirality relating to secondary structure in native and released sample was assessed using Far-UV circular dichroism spectrometry. Protein asymmetry was analysed between 185-260 nm using a Chirascan and compared to published data. The (quartz) cuvette path length used was 1 mm. Native and released protein were dialysed against $KPO_4$ buffer at a neutral pH before measurements.

ELISA

On a 96-wells ELISA plate, rTTCF was bound in 50 mM bicarbonate buffer incubating overnight at 4° C. The plate was washed with 1×Phosphate Buffered Saline (PBS) and incubated with 1% casein in PBS+Tween20 (0.05%) for 1 hour at RT followed by repeated washes. A monoclonal antibody against tetanus toxoid, 10G5, was added to each coated well and incubated. Using tetramethylbenzidine (TMB) and 2M sulfuric acid, the reaction was initiated and stopped respectively for OD450 nm measurement.

Results And Discussions

Figure 7:
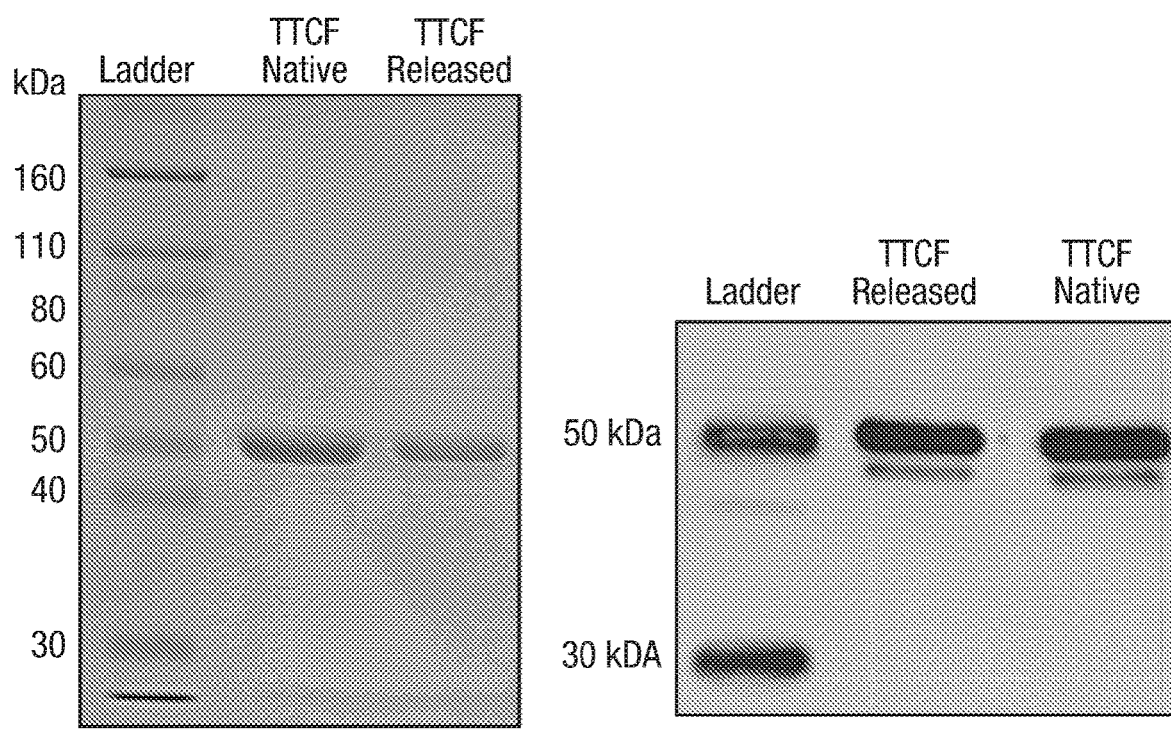
Figure 8:
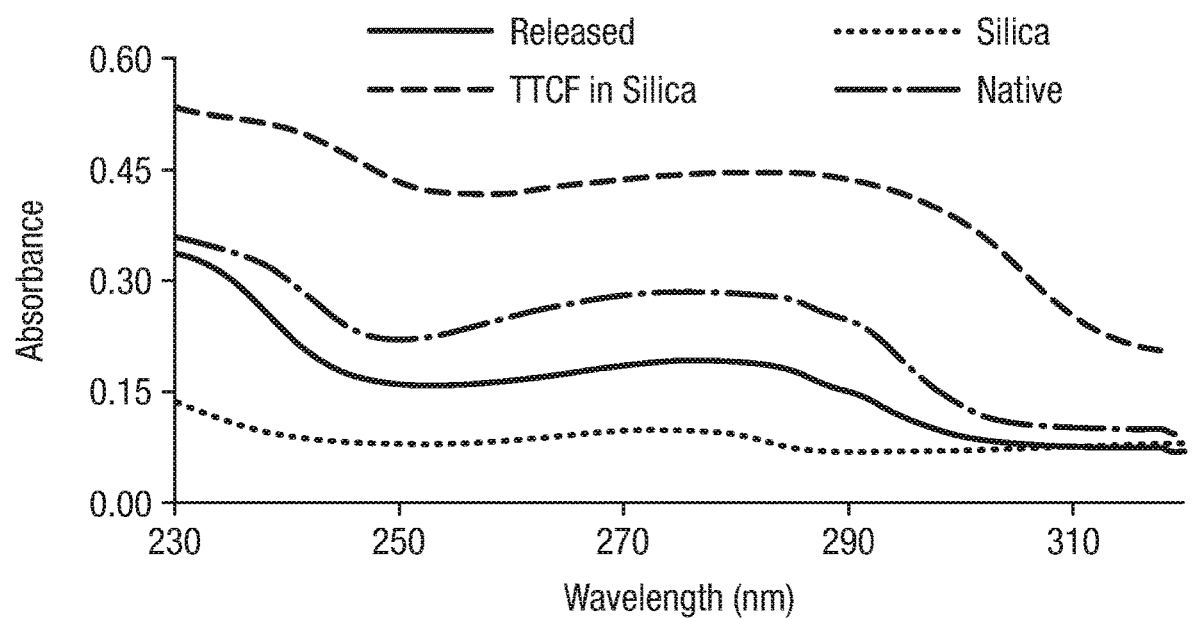

We incorporated rTTCF within a silica matrix and stored it at room temperature prior to analysis. We assessed primary, secondary and tertiary structure of rTTCF, comparing native rTTCF (purified in buffer) to rTTCF released from its protective silica matrix. Primary structure analysis of rTTCF using SDS-page and Western Blot showed that the molecular weight of the protein was unaltered following release from silica (FIG. 7). No additional bands were present which indicated that there were no degradation products present in the released sample. This is an important result as degradation would reduce the efficacy of any given vaccine. Analysis by UV-vis provided additional evidence of protein preservation as released and native sample present similar absorbance patterns (FIG. 8). Furthermore, UV-vis confirmed successful silica matrix formation around the protein as similar peaks were detected when powder material was analysed. Secondary protein structures, α-helixes and β-sheets, were detected using circular dichroism and showed matching reflectivity patterns when comparing native and released (FIG. 9). However, there is a difference in intensity and this could be explained by the presence of minute silica particles left after release, which can interfere with measurements. Alternatively, it might indicate a structural change in protein folding. However, this is unlikely since the ELISA results show equal antibody binding patterns for both released and native rTTCF which suggests the preservation of conformation relating to tertiary protein structure (FIG. 10). From these various analytical tools, it is apparent that our method does not interact or affect structural integrity or function of rTTCF. Immunogenicity of rTTCF after release from silica will have to be confirmed by carrying out in vivo animal experiments to complete this investigation.

Example 3

Tetanus toxoid C fragment (TTCF) is currently used as a vaccine component and so was interesting to use to test the integrity of this molecule after storage and heating when ensilicated and when lyophilised. An ELISA binding assay was performed on native TTCF, native TTCF heated for 2 hours at 80° C., TTCF released from ensilication and ensilicated TTCF heated for 2 hours at 80° C. and released, lyophilised TTCF and lyophilised TTCF heated for 2 hours at 80° C. and the results are shown in FIG. 11. The antibody binding capacity, measured by ELISA, of tetanus toxoid C fragment (TTCF) which has been ensilicated and stored, with or without heat treatment at 80° C., and then released back into solution, is effectively indistinguishable from the antibody binding capacity of native TTCF in solution. The binding capacity of lyophilised TTCF reconstituted into solution is slightly lower than that of native TTCF in solution. The binding capacity of lyophilised TTCF subjected to heat treatment at 80° C. (i.e. a dry bake) and then reconstituted into solution is slightly lower again. The binding capacity of unprotected TTCF subjected to heat treatment at 80° C. in solution is effectively zero due to denaturation of the protein.

The invention claimed is:

1. A biomolecule enveloped with silica, wherein the silica envelope is substantially continuous and non-porous and separates the biomolecule from surrounding conditions, wherein the silica has been deposited around the biomolecule, and wherein the biomolecule comprises a protein or polypeptide.

2. The biomolecule enveloped with silica according to claim 1, wherein the surrounding conditions are denaturing conditions, optionally selected from heat, acid pH and aging; or wherein the surrounding conditions are other molecules.

3. The biomolecule enveloped with silica according to claim 1, wherein separation from surrounding conditions prevents the biomolecule from performing its function.

4. The biomolecule enveloped with silica according to claim 1, wherein the silica envelope is water impermeable; or wherein the silica envelope comprises one or more layers of covalently bonded amorphous silica; or wherein the silica envelope is amorphous nano silica; or wherein the silica envelope prevents denaturation of the biomolecule.

5. The biomolecule enveloped with silica according to claim 1, wherein the biomolecule has secondary structure, optionally has tertiary structure and further optionally has quaternary structure; or wherein the biomolecule is a protein vaccine or a virus-like particle; or wherein the biomolecule is an antibody or fragment thereof, or is an enzyme.

6. A powder or a suspension comprising a plurality of biomolecules enveloped with silica according to claim 1.

7. An oral vaccine comprising the biomolecule enveloped with silica according to claim 1.

8. A gastric-resistant oral dosage form of a biomolecule comprising the biomolecule enveloped with silica according to claim 1.

9. A biomolecule enveloped with silica according to claim 1 for therapy or for vaccination.

10. A method of enveloping a biomolecule with silica comprising:
   a) hydrolysing a silica starting material to produce a hydrolysed silica precursor,
   b) contacting the hydrolysed silica precursor with an aqueous solution comprising a buffer and the biomolecule at a pH of ≥6, wherein the hydrolysed silica precursor in aqueous solution forms a single phase, wherein the silica precursor precipitates about the biomolecule to form a substantially continuous and non-porous envelope of covalently bonded amorphous silica about the biomolecule which separates the biomolecule from surrounding conditions, and wherein the method occurs in aqueous phase, and wherein the biomolecule comprises a protein or polypeptide.

11. The method according to claim 10, wherein the silica starting material contains silicon atoms coordinated by labile organic groups, optionally wherein the silicon atoms are coordinated by alkoxide groups or derivatives of alkoxide groups, further optionally wherein the silicon atoms are coordinated by methoxy, ethoxy, propoxy, butoxy groups or derivates thereof; or wherein the silica starting material contains tetra-ethoxy-orthosilicate (TEOS); or
wherein the hydrolysed silica precursor comprises
   a) silica monomers, and/or
   b) hydrolysed alkoxysilane or hydrolysed TEOS.

12. The method according to claim 10, wherein hydrolysing a silica starting material to produce a hydrolysed silica precursor occurs at acidic pH, optionally wherein the acidic pH≤4.0, 3.5, 3.0, 2.5 or 2.0.

13. The method according to claim 10, wherein the hydrolysed silica precursor in aqueous solution has a viscosity similar to water.

14. The method according to claim 10, wherein contacting the hydrolysed silica precursor with an aqueous solution comprising the biomolecule occurs at a pH in the range of 6.5≤pH≥7.5, optionally wherein the pH is about 7.

15. The method according to claim 10, wherein enveloping the biomolecule with silica prevents denaturation of the biomolecule.

16. The method according to claim 10, wherein the aqueous solution comprising the biomolecule and the buffer and has a pH in the range of 6.5≤pH≥7.5, optionally wherein the pH is about 7; wherein the aqueous solution comprising the biomolecule has a concentration of the biomolecule which is less than that which causes spontaneous aggregation of the biomolecule.

17. A method of reducing biomolecule denaturation in non-physiological conditions comprising enveloping the biomolecule with silica, the enveloping comprising contacting a hydrolysed silica precursor with an aqueous solution comprising the biomolecule, wherein the silica precursor precipitates about the biomolecule to form a substantially continuous and non-porous silica envelope which separates the biomolecule from surrounding conditions, wherein the method occurs in aqueous phase, and wherein the biomolecule comprises a protein or polypeptide; or
a method of transporting and/or storing a biomolecule, comprising
   a) obtaining the biomolecule enveloped with silica, wherein the silica envelope is substantially continuous and non-porous and separates the biomolecule from surrounding conditions, wherein the silica has been deposited around the biomolecule, and wherein the biomolecule comprises a protein or polypeptide, and
   b) transporting the biomolecule from a first location to a second location and/or storing the biomolecule,
   wherein at least a portion of the transporting and/or storing occurs in the absence of a cold-chain; or
a method of providing a gastric resistant coating to a biomolecule comprising contacting a hydrolysed silica precursor with an aqueous solution comprising the biomolecule, wherein the silica precursor precipitates about the biomolecule to form a substantially continuous and non-porous silica envelope which separates the biomolecule from surrounding conditions and which acts as the gastric resistant coat, wherein the method occurs in aqueous phase, and wherein the biomolecule comprises a protein or polypeptide.

18. The method according to claim 17, wherein the biomolecule is a therapeutic agent.

19. A method of vaccination comprising administering to a subject in need thereof, a vaccine comprising a biomolecule enveloped with silica, wherein the silica envelope is substantially continuous and non-porous and separates the biomolecule from surrounding conditions, wherein the silica has been deposited around the biomolecule, and wherein the biomolecule comprises a protein or polypeptide; or a method of vaccination comprising administration to a subject in need thereof, a biomolecule with secondary or higher order structure, by a) oral administration of the biomolecule enveloped with silica, wherein the silica envelope is substantially continuous and non-porous and separates the biomolecule from surrounding conditions, wherein the silica has been deposited around the biomolecule, and wherein the biomolecule comprises a protein or polypeptide, or b) release of the biomolecule from a substantially continuous and non-porous silica envelope which separates the biomolecule from surrounding conditions, wherein the silica has been deposited around the biomolecule, and wherein the biomolecule comprises a protein or polypeptide, followed by re-formulation of the biomolecule and injection into the subject.

20. The method according to claim 19, wherein the biomolecule is a protein vaccine or a virus-like particle; or wherein the biomolecule is an antibody or fragment thereof, or an enzyme.

21. The method according to claim 19, wherein the administration is oral administration.

* * * * *